US010420666B2

(12) United States Patent
Baym et al.

(10) Patent No.: US 10,420,666 B2
(45) Date of Patent: Sep. 24, 2019

(54) APPARATUS, SYSTEM, AND METHOD FOR CONTROLLING MOVEMENT OF AN ORTHOPEDIC JOINT PROSTHESIS IN A MAMMALIAN SUBJECT

(71) Applicant: Elwha LLC, Bellevue, WA (US)

(72) Inventors: Michael H. Baym, Cambridge, MA (US); Roderick A. Hyde, Redmond, WA (US); Elizabeth A. Sweeney, Seattle, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 778 days.

(21) Appl. No.: 13/858,738

(22) Filed: Apr. 8, 2013

(65) Prior Publication Data

US 2014/0303540 A1    Oct. 9, 2014

(51) Int. Cl.
*A61F 5/01* (2006.01)
*A61B 5/00* (2006.01)
(Continued)

(52) U.S. Cl.
CPC .......... *A61F 5/0102* (2013.01); *A61B 5/0031* (2013.01); *A61B 5/1114* (2013.01);
(Continued)

(58) Field of Classification Search
CPC .. A61F 2/28; A61F 2/2814; A61F 2/30; A61F 2/32; A61F 2/38; A61F 2/384;
(Continued)

(56) References Cited

U.S. PATENT DOCUMENTS 3,995,324 A    12/1976   Burch
4,135,503 A     1/1979   Romano
(Continued)

FOREIGN PATENT DOCUMENTS

DE    102010022878 A1   12/2011
EP      2 335 651 A1     6/2011
(Continued)

OTHER PUBLICATIONS

PCT International Search Report; International App. No. PCT/US2014/032689; dated Aug. 6, 2014; pp. 1-5.
(Continued)

*Primary Examiner* — Thomas Sweet
*Assistant Examiner* — Christie L Bahena
(74) *Attorney, Agent, or Firm* — Daniel J. Honz; Advent, LLP

(57) ABSTRACT

Apparatus, system, and method are disclosed herein for controlling movement of an artificial orthopedic joint prosthesis in a mammalian subject. The apparatus, system, or method includes an orthopedic brace configured to control movement of an orthopedic joint prosthesis. The apparatus, system, or method includes one or more sensors and one or more controllers in communication with the one or more sensors. The one or more sensors are configured to detect a change in an orientation of a subject's position in an environment and configured to detect one or more alignment orientations of the orthopedic joint prosthesis.

16 Claims, 10 Drawing Sheets

(51) Int. Cl.

| | | |
|---|---|---|
| *A61B 5/11* | (2006.01) | |
| *A61B 8/08* | (2006.01) | |
| *A61B 8/00* | (2006.01) | |
| *A61B 5/03* | (2006.01) | |
| *A61F 2/36* | (2006.01) | |

(52) U.S. Cl.
CPC .......... *A61B 5/4528* (2013.01); *A61B 5/4571* (2013.01); *A61B 5/4851* (2013.01); *A61B 5/6811* (2013.01); *A61B 5/6812* (2013.01); *A61B 8/0875* (2013.01); *A61B 8/4227* (2013.01); *A61B 8/4254* (2013.01); *A61B 5/03* (2013.01); *A61B 8/523* (2013.01); *A61F 2/36* (2013.01)

(58) Field of Classification Search
CPC .... A61F 2/3836; A61F 2/3859; A61F 2/3886; A61F 2/40; A61F 2/42; A61F 2/4202; A61F 2/4225; A61F 2/4241; A61F 2/72; A61F 5/0106; A61F 5/0125; A61F 5/0102; A61F 5/0109; A61F 5/1093; A61F 5/04; A61B 5/01; A61B 5/0102; A61B 5/0106; A61B 5/0109; A61B 5/117; A61B 5/04; A61B 5/0002; A61B 5/0004; A61B 5/0024; A61B 5/0048; A61B 5/0053; A61B 5/1038; A61B 5/103; A61B 5/1071; A61B 5/1114; A61B 5/1116; A61B 5/1121; A61B 5/112; A61B 5/1123; A61B 5/6812; A61B 5/681; A61B 5/6879; A61B 5/6891
See application file for complete search history.

(56) References Cited

U.S. PATENT DOCUMENTS

| | | |
|---|---|---|
| 4,552,135 A | 11/1985 | Racz et al. |
| 4,608,998 A | 9/1986 | Murdock |
| 4,813,435 A | 3/1989 | Arms |
| 5,226,874 A | 7/1993 | Heinz et al. |
| 5,346,461 A | 9/1994 | Heinz et al. |
| 5,421,810 A | 6/1995 | Davis et al. |
| 5,437,617 A | 8/1995 | Heinz et al. |
| 5,474,088 A | 12/1995 | Zaharkin et al. |
| 5,533,519 A | 7/1996 | Radke et al. |
| 5,558,627 A | 9/1996 | Singer et al. |
| 5,624,383 A | 4/1997 | Hazard et al. |
| 5,628,721 A | 5/1997 | Arnold et al. |
| 5,711,746 A | 1/1998 | Carlson |
| 5,935,171 A | 8/1999 | Schneider et al. |
| 6,110,130 A | 8/2000 | Kramer |
| 6,245,109 B1 | 6/2001 | Mendes et al. |
| 6,331,170 B1 | 12/2001 | Ordway |
| 6,447,448 B1 | 9/2002 | Ishikawa et al. |
| 6,540,707 B1 | 4/2003 | Stark et al. |
| 6,589,195 B1 | 7/2003 | Schwenn et al. |
| 6,733,467 B2 | 5/2004 | Kania |
| 6,761,741 B2 | 7/2004 | Iesaka |
| 7,048,098 B1 | 5/2006 | Moradian |
| 7,190,273 B2 | 3/2007 | Liao et al. |
| 7,413,554 B2 | 8/2008 | Kobayashi et al. |
| 7,507,215 B2 | 3/2009 | Ryan |
| 7,575,602 B2 | 8/2009 | Amirouche et al. |
| 7,922,773 B1 | 4/2011 | Kuiken |
| 7,947,862 B2 | 5/2011 | Livorsi |
| 7,955,280 B2 | 6/2011 | Radinsky et al. |
| 8,048,172 B2 | 11/2011 | Jónsson et al. |
| 8,057,410 B2 | 11/2011 | Angold et al. |
| 8,058,823 B2 | 11/2011 | Horst et al. |
| 2001/0020143 A1 | 9/2001 | Stark et al. |
| 2002/0022792 A1 | 2/2002 | Kania |
| 2002/0103435 A1 | 8/2002 | Mault |
| 2002/0143279 A1 | 10/2002 | Porier et al. |
| 2003/0135134 A1 | 7/2003 | Chase et al. |
| 2004/0064195 A1 | 4/2004 | Herr |
| 2004/0106881 A1 | 6/2004 | McBean et al. |
| 2004/0267379 A1 | 12/2004 | Pasolini |
| 2005/0010301 A1 | 1/2005 | Disilvestro et al. |
| 2005/0012610 A1 | 1/2005 | Liao et al. |
| 2005/0251079 A1 | 11/2005 | Carvey et al. |
| 2006/0009856 A1 | 1/2006 | Sherman et al. |
| 2006/0047283 A1 | 3/2006 | Evans, III et al. |
| 2006/0069447 A1 | 3/2006 | DiSilvestro et al. |
| 2006/0094989 A1 | 5/2006 | Scott et al. |
| 2006/0096818 A1 | 5/2006 | Moradian |
| 2006/0130594 A1 | 6/2006 | Ikeuchi |
| 2006/0135883 A1 | 6/2006 | Jonsson et al. |
| 2006/0189899 A1 | 8/2006 | Flaherty et al. |
| 2006/0200057 A1 | 9/2006 | Sterling |
| 2006/0260620 A1 | 11/2006 | Kazerooni et al. |
| 2006/0271199 A1 | 11/2006 | Johnson |
| 2007/0004994 A1* | 1/2007 | Sherman ............. A61B 5/0031 602/26 |
| 2008/0071386 A1 | 3/2008 | McBean et al. |
| 2008/0132818 A1 | 6/2008 | Livorsi |
| 2008/0223131 A1 | 9/2008 | Vannucci et al. |
| 2008/0262347 A1 | 10/2008 | Batchelder et al. |
| 2008/0281235 A1 | 11/2008 | Cowin |
| 2009/0227925 A1 | 9/2009 | McBean et al. |
| 2009/0259319 A1 | 10/2009 | DiSilvestro et al. |
| 2009/0281235 A1 | 11/2009 | Harris, III et al. |
| 2009/0299480 A1 | 12/2009 | Gilbert et al. |
| 2009/0312807 A1 | 12/2009 | Boudreault et al. |
| 2010/0100011 A1 | 4/2010 | Roche |
| 2010/0198067 A1 | 8/2010 | Mahfouz et al. |
| 2010/0198124 A1 | 8/2010 | Bhugra |
| 2010/0324698 A1 | 12/2010 | Sverrisson et al. |
| 2012/0184887 A1 | 7/2012 | Wynne et al. |
| 2012/0191206 A1 | 7/2012 | Stein et al. |
| 2012/0221119 A1 | 8/2012 | Goldfarb et al. |
| 2013/0041477 A1 | 2/2013 | Sikdar et al. |
| 2013/0190669 A1* | 7/2013 | Rokosz ................ A61F 5/0125 602/16 |
| 2013/0211259 A1 | 8/2013 | Komistek et al. |

FOREIGN PATENT DOCUMENTS

| | | |
|---|---|---|
| WO | WO 97/15249 | 5/1997 |
| WO | WO 2013/190495 A1 | 12/2013 |

OTHER PUBLICATIONS

Bamberg et al.; "Gait Analysis Using a Shoe-Integrated Wireless Sensor System"; IEEE Transactions on Information Technology in Biomedicine; Jul. 2008; pp. 413-423; vol. 12, No. 4; IEEE.

Kobetic et al.; "Development of hybrid orthosis for standing, walking, and stair climbing after spinal cord injury"; Journal of Rehabilitation Research & Development; Jan. 13, 2009; pp. 447-462; vol. 46, No. 3.

Lima, Dulcey; "Orthotic Management of Hip Dislocation Using a Newport 4 Hip Orthosis"; Clinical Report; 4 pgs.; last accessed Nov. 13, 2012.

Lion Precision; TechNote LT05-0011; "Differences Between Capacitive and Eddy-Current Sensors"; Aug. 7, 2012; pp. 1-9.

Liu et al.; "Visual Estimation of Lower Limb Motion Using Physical and Virtual Sensors"; Proceedings of the 2010 IEEE International Conference on Information and Automation Jun. 20-23, 2010; Harbin, China; pp. 179-184; IEEE.

MOOG A085 Series Servoactuators; two pages of Specification; last accessed Sep. 25, 2012.

Noel et al.; "Using an electrohydraulic ankle foot orthosis to study modifications in feedforward control during locomotor adaptation to force fields applied in stance"; Journal of NeuroEngineering and Rehabilitation; Jun. 3, 2009; pp. 1-11; vol. 6, No. 16; BioMed Central Ltd.

Orthomerica the Global Orthotic Solution; "Newport 4 Hip System"; bearing a date of 2008; two pages; Orthomerica Products, Inc.
Physical Therapy in Fernley for Hip; "Artificial Hip Dislocation Precautions"; pp. 1-8; printed on Sep. 19, 2012; Fernley Physical Therapy.

(56) References Cited

OTHER PUBLICATIONS

Sashima et al.; "Toward Mobile Sensor Fusion Platform for Context-Aware Services"; Intelligent and Biosensors; published Jan. 1, 2010; Chapter 3; pp. 67-82; Intech; Croatia.

Sashima et al.; Consorts-S: A Mobile Sensing Platform for Context-Aware Services; National Institute of Advanced Industrial Science and Technology; bearing a date of 2008; pp. 417-422; IEEE.

Sazonov et al.; "Monitoring of Posture Allocations and Activities by a Shoe-Based Wearable Sensor"; IEEE Transactions on Biomedical Engineering; Apr. 2011; pp. 983-990; vol. 58, No. 4.

Extended European Search Report; European App. No. EP 14 78 3126; dated Dec. 20, 2016 (received by our Agent on Dec. 22, 2016); pp. 1-8.

* cited by examiner

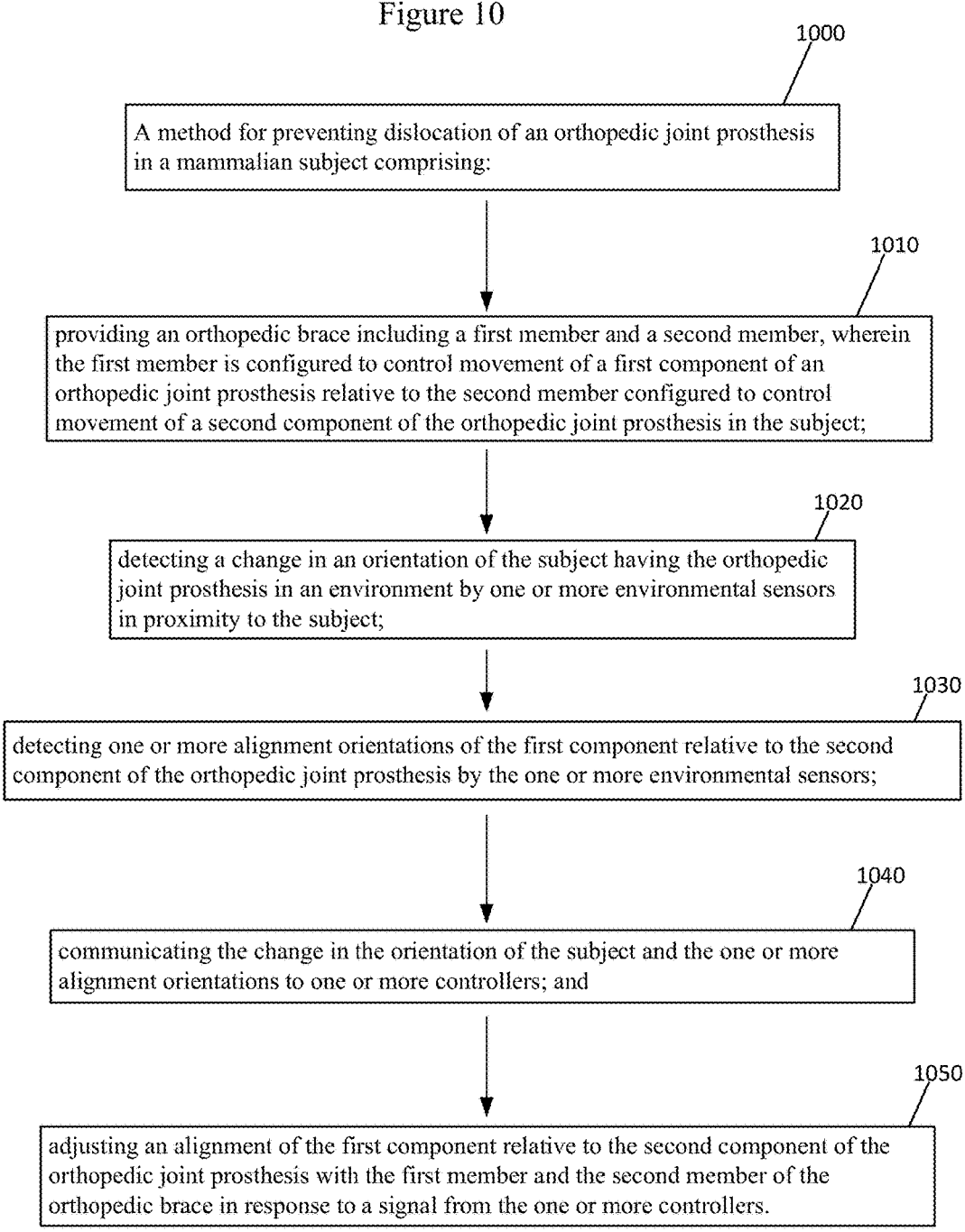

APPARATUS, SYSTEM, AND METHOD FOR CONTROLLING MOVEMENT OF AN ORTHOPEDIC JOINT PROSTHESIS IN A MAMMALIAN SUBJECT

CROSS-REFERENCE TO RELATED APPLICATIONS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)). In addition, the present application is related to the "Related applications," if any, listed below.

PRIORITY APPLICATIONS

None.

RELATED APPLICATIONS

U.S. patent application Ser. No. 13/858,652, entitled Apparatus, System, and Method for Controlling Movement of an Orthopedic Joint Prosthesis in a Mammalian Subject, naming Michael H. Baym, Roderick A. Hyde, Elizabeth A. Sweeney and Lowell L. Wood, Jr. as inventors, filed 8 Apr. 2013, is related to the present application.

U.S. patent application Ser. No. 13/858,699, entitled Apparatus, System, and Method for Controlling Movement of an Orthopedic Joint Prosthesis in a Mammalian Subject, naming Michael H. Baym, Roderick A. Hyde, Elizabeth A. Sweeney and Lowell L. Wood, Jr. as inventors, filed 8 Apr. 2013, is related to the present application.

If the listings of applications provided above are inconsistent with the listings provided via an ADS, it is the intent of the Applicant to claim priority to each application that appears in the Priority applications section of the ADS and to each application that appears in the Priority applications section of this application.

All subject matter of the Priority applications and the Related applications and of any and all parent, grandparent, great-grandparent, etc. applications of the Priority applications and the Related applications, including any priority claims, is incorporated herein by reference to the extent such subject matter is not inconsistent herewith.

SUMMARY

Apparatus, system, and method are disclosed herein for controlling movement of an orthopedic joint prosthesis in a mammalian subject. A method is disclosed for preventing dislocation of an orthopedic joint prosthesis in the mammalian subject. The apparatus, system, or method includes an orthopedic brace including a first member and a second member, wherein the first member is configured to control movement of a first component of an orthopedic joint prosthesis relative to a second component of the orthopedic joint prosthesis. The apparatus, system, or method includes one or more sensors and one or more controllers in communication with the one or more sensors. In an embodiment, the one or more sensors are configured to be remote from the orthopedic joint prosthesis, wherein the one or more sensors are configured to detect one or more alignment orientations of the first component relative to the second component of the orthopedic joint prosthesis. The one or more alignment orientations may include one or more of angular alignment and linear alignment. In an embodiment, the one or more sensors are configured to contact the orthopedic joint prosthesis, wherein the one or more sensors are configured to detect one or more alignment orientations of the first component relative to the second component of the orthopedic joint prosthesis. In an embodiment, one or more environmental sensors are configured to be remote from the orthopedic joint prosthesis or are configured to be in contact with the orthopedic joint prosthesis. The one or more environmental sensors are configured to detect a change in an orientation of a position of a subject wearing the orthopedic joint prosthesis relative to the subject's position in an environment. The one or more environmental sensors are configured to detect one or more alignment orientations of the first component relative to the second component of the orthopedic joint prosthesis.

An apparatus is disclosed that includes an orthopedic brace including a first member and a second member, wherein the first member is configured to control movement of a first component of an orthopedic joint prosthesis relative to the second member configured to control movement of a second component of the orthopedic joint prosthesis; one or more sensors configured to detect a change in an orientation of a subject's position in an environment and configured to detect one or more alignment orientations of the first component relative to the second component of the orthopedic joint prosthesis; one or more controllers in communication with the one or more sensors, wherein the one or more sensors are configured to report to the one or more controllers the one or more alignment orientations and the change in the orientation of the subject's position in the environment, and the one or more controllers are configured to control activity of the first member relative to the second member of the orthopedic brace, wherein the orthopedic brace is configured to adjust the one or more alignment orientations of the first component relative to the second component of the orthopedic joint prosthesis.

The one or more sensors may be configured to detect the one or more alignment orientations of the orthopedic joint prosthesis based upon detecting one or more alignment orientations of the orthopedic brace. The one or more sensors may be configured to detect the one or more alignment orientations of the orthopedic joint prosthesis based upon detecting one or more alignment orientations of portions of a human body containing the orthopedic joint prosthesis. In some embodiments, the apparatus may include one or more force-applying elements configured to control movement of the first member relative to the second member, wherein the one or more force-applying elements in response to the one or more controllers are configured to permit unrestrained motion of the orthopedic joint prosthesis under a first set of the one or more alignment orientations and are configured to permit restrained motion of the orthopedic joint prosthesis under a second set of the one or more alignment orientations. The one or more sensors may be configured to be remote from the orthopedic joint prosthesis. The one or more sensors may be configured to be in contact with the orthopedic joint prosthesis. The first set of the one or more alignment orientations may include physiologically normal alignment of the orthopedic joint prosthesis. The second set of the one or more alignment orientations may include physiologically abnormal alignment of the orthopedic joint prosthesis. The second set of the one or more alignment orientations may include a misalignment of the first component relative to the second component of the orthopedic joint prosthesis. The second set of the one or more alignment orientations may include a separation of the first component relative to the second component of the orthopedic joint prosthesis. The restrained motion may include a stopped motion of the orthopedic joint prosthesis. The restrained motion may include a motion from the second set of the one or more alignment orientations towards the first set of the one or more alignment orientations. The restrained motion may include a reduction of one or more alignment differences between the second set of the one or more alignment orientations and the first set of the one or more alignment orientations.

In some embodiments, the one or more sensors may include one or more imaging devices. The one or more sensors may include one or more pressure sensors on furniture. The one or more sensors may include one or more accelerometers. The one or more sensors may include one or more antiskid shoes. The one or more sensors may be configured to be located within an environment of the orthopedic brace. The one or more sensors may be configured to be located on the floor, wall or furniture within the environment. The one or more sensors may be configured to detect the one or more alignment orientations of the orthopedic joint prosthesis based upon detecting one or more alignment orientations of the orthopedic brace. The one or more sensors may be configured to detect the one or more alignment orientations of the orthopedic joint prosthesis based upon detecting one or more alignment orientations of portions of a human body containing the orthopedic joint prosthesis. The one or more sensors may be configured to measure one or more properties of tissue of a mammalian subject surrounding the orthopedic joint prosthesis. The one or more sensors may be configured to measure strain on one or more of ligament, muscle, or bone of the mammalian subject surrounding the orthopedic joint prosthesis. The one or more sensors may include one or more of electrical energy sensors, magnetic sensors, electromagnetic energy sensors, optical sensors, or sonic energy sensors. The one or more sonic energy sensors may include one or more ultrasonic sensors. The one or more ultrasonic sensors may be configured to determine a separation between the first component and the second component of the orthopedic joint prosthesis. The one or more magnetic sensors may be configured to determine a separation between the first component and the second component of the orthopedic joint prosthesis. The one or more magnetic sensors may be configured to determine a movement between the first component and the second component of the orthopedic joint prosthesis. The one or more ultrasonic sensors may be configured to determine a movement between the first component and the second component of the orthopedic joint prosthesis. The one or more electromagnetic energy sensors may include one or more of radio, visible, ultraviolet, infrared, or near infrared wavelength sensors. The one or more radio wavelength sensors may be configured to determine a separation between the first component and the second component of the orthopedic joint prosthesis. The one or more radio wavelength sensors may be configured to determine a movement between the first component and the second component of the orthopedic joint prosthesis. The one or more electromagnetic energy sensors may include one or more interferometric sensors configured to detect a separation between the first component and the second component of the orthopedic joint prosthesis. The one or more sensors may be configured to detect one or more of positioning, disposition, attitude, movement, friction or temperature of the orthopedic joint prosthesis.

The one or more sensors may be configured to detect one or more of pressure, angle, motion, strain, flexion, extension, position, force, speed, acceleration, or temperature of the orthopedic joint prosthesis. The one or more sensors may be configured to detect one or more of chemical change or biological change in a mammalian subject. The one or more sensors may include one or more capacitive sensors. The one or more sensors may be configured to detect a separation between the first component and the second component of the orthopedic joint prosthesis. The orthopedic brace may include one or more mechanical or rheological mechanisms. The one or more environmental sensors may be configured to inform the one or more sensors or the one or more controllers. The one or more sensors or the one or more controllers may be configured to be activated in response to a signal from the one or more environmental sensors. The apparatus may include a power source. The apparatus may include a receiver configured to receive wireless signals from the one or more environmental sensors. The apparatus may include a receiver configured to receive wire-based signals from the one or more environmental sensors. The apparatus may include a transmitter configured to transmit a request for data from the one or more environmental sensors. The apparatus may include the one or more controllers configured to use information from a model of one or more of a limb or a joint of the mammalian subject, wherein the one or more controllers are configured to predict future actions or consequences of movement of the brace. The orthopedic brace may include a mechanism external to a mammalian subject. The orthopedic brace may include a mechanism internal to a mammalian subject.

A system is disclosed that includes an orthopedic brace including a first member and a second member, wherein the first member is configured to control movement of a first component of an orthopedic joint prosthesis relative to the second member configured to control movement of a second component of the orthopedic joint prosthesis; one or more sensors configured to detect a change in an orientation of a subject's position in an environment and configured to detect one or more alignment orientations of the first component relative to the second component of the orthopedic joint prosthesis; one or more controllers in communication with the one or more sensors, wherein the one or more sensors are configured to report to the one or more controllers the one or more alignment orientations and the change in the orientation of the subject's position in the environment, and the one or more controllers are configured to control activity of the first member relative to the second member of the orthopedic brace, wherein the orthopedic brace is configured to adjust the one or more alignment orientations of the first component relative to the second component of the orthopedic joint prosthesis.

A method for preventing dislocation of an orthopedic joint prosthesis in a mammalian subject apparatus is disclosed that includes providing an orthopedic brace including a first member and a second member, wherein the first member is configured to control movement of a first component of an orthopedic joint prosthesis relative to the second member configured to control movement of a second component of the orthopedic joint prosthesis in the subject; detecting an orientation of the subject having the orthopedic joint prosthesis in an environment by one or more sensors in proximity to the subject; detecting one or more alignment orientations of the first component relative to the second component of the orthopedic joint prosthesis by the one or more sensors; communicating on the orientation of the subject and the one or more alignment orientations to one or more controllers; and adjusting an alignment of the first component relative to the second component of the orthopedic joint prosthesis in response to a signal from the one or more controllers to the first member and the second member of the orthopedic brace.

In some embodiments, the method may include detecting the one or more alignment orientations of the orthopedic joint prosthesis based upon detecting one or more alignment orientations of the orthopedic brace by the one or more sensors in proximity to the subject. The method may include detecting one or more alignment orientations of portions of a human body containing the orthopedic joint prosthesis by the one or more sensors in proximity to the subject. The method may include restraining motion of the orthopedic joint prosthesis by the orthopedic brace under a first set of the one or more alignment orientations, and permitting unrestrained motion of the orthopedic joint prosthesis by the orthopedic brace under a second set of the one or more alignment orientations. The first set of the one or more alignment orientations may include physiologically normal alignment of the orthopedic joint prosthesis. The second set of the one or more alignment orientations may include physiologically abnormal alignment of the orthopedic joint prosthesis. The second set of the one or more alignment orientations may include a misalignment of the first component relative to the second component. The second set of the one or more alignment orientations may include a separation of the first component relative to the second component. The method may include restraining motion to stop motion of the orthopedic joint prosthesis. The method may include restraining motion from the second set of the one or more alignment orientations towards the first set of the one or more alignment orientations. The may include restraining motion to reduce one or more alignment differences between the second set of the one or more alignment orientations and the first set of the one or more alignment orientations.

In some embodiments, the one or more sensors may include one or more imaging devices. The one or more sensors may include one or more pressure sensors on furniture. The one or more sensors may include one or more accelerometers. The one or more sensors may include one or more antiskid shoes. In some embodiments, the method may include controlling movement of the first member relative to the second member of the orthopedic brace by one or more force-applying elements, wherein the one or more force-applying elements in response to the one or more controllers are configured to permit unrestrained motion of the orthopedic joint prosthesis under a first set of the one or more alignment orientations and are configured to permit restrained motion of the orthopedic joint prosthesis under a second set of the one or more alignment orientations. The method may include controlling application of force to the orthopedic joint prosthesis by the one or more force-applying elements by the one or more controllers. The one or more force-applying elements may be configured to control movement of the first component relative to the second component of the orthopedic joint prosthesis. The one or more force-applying elements may be configured to exert linear force or rotational force on the orthopedic joint prosthesis.

The method may include locating the one or more sensors within an environment of the orthopedic brace. The one or more sensors may be configured to be located on the floor, wall or furniture within the environment. The one or more sensors may be configured to detect the one or more alignment orientations of the orthopedic joint prosthesis based upon detecting one or more alignment orientations of the orthopedic brace. The one or more sensors may be configured to detect the one or more alignment orientations of the orthopedic joint prosthesis based upon detecting one or more alignment orientations of portions of a human body containing the orthopedic joint prosthesis.

In some embodiments, the method may include measuring one or more properties of the tissue surrounding the orthopedic joint prosthesis with the one or more sensors. The method may include measuring strain on one or more of ligament, muscle, or bone of the mammalian subject surrounding the orthopedic joint prosthesis with the one or more sensors. The method may include detecting one or more of pressure, angle, motion, strain, flexion, extension, position, force, speed, acceleration, or temperature of the orthopedic joint prosthesis with the one or more sensors. The method may include detecting one or more of chemical change or biological change in a mammalian subject with the one or more sensors. The method may include detecting one or more of electrical energy, magnetic energy, electromagnetic energy, optical energy, or sonic energy by the one or more sensors. The method may include detecting the sonic energy by one or more ultrasonic sensors. The method may include determining a separation between the first component and the second component of the orthopedic joint prosthesis with the one or more ultrasonic sensors. The method may include determining a movement between the first component and the second component of the orthopedic joint prosthesis with the one or more ultrasonic sensors. The method may include determining a separation between the first component and the second component of the orthopedic joint prosthesis with one or more magnetic sensors. The method may include determining a movement between the first component and the second component of the orthopedic joint prosthesis with one or more magnetic sensors. The one or more electromagnetic energy sensors may include one or more of radio, visible, ultraviolet, infrared, or near infrared wavelength sensors. The method may include determining a separation between the first component and the second component of the orthopedic joint prosthesis with the one or more radio wavelength sensors. The method may include determining a movement between the first component and the second component of the orthopedic joint prosthesis with the one or more radio wavelength sensors. The method may include detecting one or more of positioning, disposition, attitude, movement, friction or temperature of the orthopedic joint prosthesis with the one or more second sensors.

In some embodiments, the method may include informing the one or more sensors or the one or more controllers by a signal from the one or more environmental sensors. The method may include activating the one or more sensors or the one or more controllers in response to a signal from the one or more environmental sensors. The method may include predicting future actions or consequences of movement of the orthopedic brace with one or more controllers configured to use information from a model of one or more of a limb or a joint of the mammalian subject. The method may include receiving wireless signals at a receiver from the one or more environmental sensors. The method may include receiving wire-based signals at a receiver from the one or more environmental sensors. The method may include transmitting a request from a transmitter for data from the one or more environmental sensors.

A device is disclosed that includes a system including a signal-bearing medium including, one or more instructions for treatment of a subject with an orthopedic brace including device including one or more instructions for receiving data for a first member and a second member, wherein the first member is configured to control movement of a first component of an orthopedic joint prosthesis relative to the second member configured to control movement of a second component of the orthopedic joint prosthesis; one or more instructions for receiving data from one or more sensors configured to detect a change in an orientation of a subject's position in an environment and configured to detect one or more alignment orientations of the first component relative to the second component of the orthopedic joint prosthesis; one or more instructions for receiving data from one or more controllers in communication with the one or more sensors, wherein the one or more sensors are configured to report to the one or more controllers the one or more alignment orientations and the change in the orientation of the subject's position in the environment, and the one or more controllers are configured to control activity of the first member relative to the second member of the orthopedic brace, wherein the orthopedic brace is configured to adjust the one or more alignment orientations of the first component relative to the second component of the orthopedic joint prosthesis.

A system is disclosed that includes at least one computer program included on a computer-readable medium for use with at least one computer system wherein the computer program includes a plurality of instructions including, one or more instructions for treatment of a subject with an orthopedic brace including device including one or more instructions for receiving data for a first member and a second member, wherein the first member is configured to control movement of a first component of an orthopedic joint prosthesis relative to the second member configured to control movement of a second component of the orthopedic joint prosthesis; one or more instructions for receiving data from one or more sensors configured to detect a change in an orientation of a subject's position in an environment and configured to detect one or more alignment orientations of the first component relative to the second component of the orthopedic joint prosthesis; one or more instructions for receiving data from one or more controllers in communication with the one or more sensors, wherein the one or more sensors are configured to report to the one or more controllers the one or more alignment orientations and the change in the orientation of the subject's position in the environment, and the one or more controllers are configured to control activity of the first member relative to the second member of the orthopedic brace, wherein the orthopedic brace is configured to adjust the one or more alignment orientations of the first component relative to the second component of the orthopedic joint prosthesis.

A system is disclosed that includes at least one computer program included on a computer-readable medium for use with at least one computer system wherein the at least one computer system includes a plurality of circuitry including, an orthopedic brace including circuitry for a first member and a second member, wherein the first member is configured to control movement of a first component of an orthopedic joint prosthesis relative to the second member configured to control movement of a second component of the orthopedic joint prosthesis; circuitry for one or more sensors configured to detect a change in an orientation of a subject's position in an environment and configured to detect one or more alignment orientations of the first component relative to the second component of the orthopedic joint prosthesis, and the one or more environmental sensors are configured to measure a change in the one or more alignment orientations of the first component relative to the second component of the orthopedic joint prosthesis; circuitry for one or more controllers in communication with the one or more sensors, wherein the one or more sensors are configured to report to the one or more controllers the one or more alignment orientations and the change in the orientation of the subject's position in the environment, and the one or more controllers are configured to control activity of the first member relative to the second member of the orthopedic brace, wherein the orthopedic brace is configured to adjust the one or more alignment orientations of the first component relative to the second component of the orthopedic joint prosthesis.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 10 is a schematic of a diagrammatic view of a method for preventing dislocation of an orthopedic joint prosthesis in a mammalian subject.

DETAILED DESCRIPTION

Figure 1:
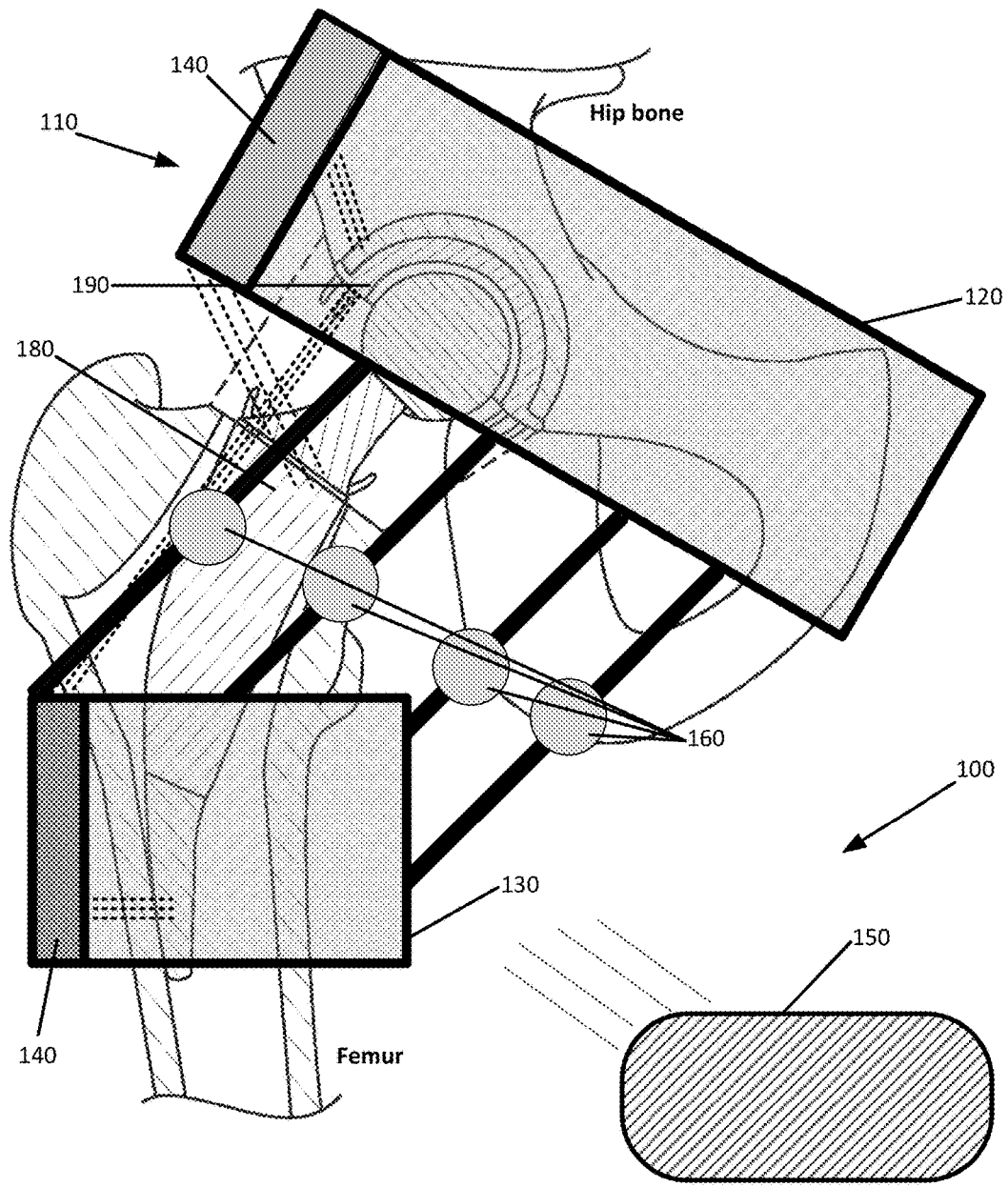
FIG. 1 is a schematic of a diagrammatic view of an apparatus including an orthopedic brace and one or more sensors configured to be remote from an orthopedic joint prosthesis.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Apparatus, system, and method are disclosed herein for controlling movement of an orthopedic joint prosthesis in a mammalian subject. A method is disclosed for preventing dislocation of an orthopedic joint prosthesis in the mammalian subject. The apparatus, system, or method includes an orthopedic brace including a first member and a second member, wherein the first member is configured to control movement of a first component of an orthopedic joint prosthesis relative to a second component of the orthopedic joint prosthesis. The apparatus, system, or method includes one or more sensors and one or more controllers in communication with the one or more sensors. In an embodiment, the one or more sensors are configured to be remote from the orthopedic joint prosthesis, wherein the one or more sensors are configured to detect one or more alignment orientations of the first component relative to the second component of the orthopedic joint prosthesis. The one or more alignment orientations may include one or more of angular alignment and linear alignment. In an embodiment, the one or more sensors are configured to contact the orthopedic joint prosthesis, wherein the one or more sensors are configured to detect one or more alignment orientations of the first component relative to the second component of the orthopedic joint prosthesis. In an embodiment, one or more environmental sensors are configured to be remote from the orthopedic joint prosthesis or are configured to be in contact with the orthopedic joint prosthesis. The one or more environmental sensors are configured to detect a change in an orientation of a position of a subject wearing the orthopedic joint prosthesis relative to the subject's position in an environment. The one or more environmental sensors are configured to detect one or more alignment orientations of the first component relative to the second component of the orthopedic joint prosthesis.

An apparatus is disclosed that includes an orthopedic brace including a first member and a second member, wherein the first member is configured to control movement of a first component of an orthopedic joint prosthesis relative to the second member configured to control movement of a second component of the orthopedic joint prosthesis; one or more sensors configured to detect a change in an orientation of a subject's position in an environment and configured to detect one or more alignment orientations of the first component relative to the second component of the orthopedic joint prosthesis; one or more controllers in communication with the one or more sensors, wherein the one or more sensors are configured to report to the one or more controllers the one or more alignment orientations and the change in the orientation of the subject's position in the environment, and the one or more controllers are configured to control activity of the first member relative to the second member of the orthopedic brace, wherein the orthopedic brace is configured to adjust the one or more alignment orientations of the first component relative to the second component of the orthopedic joint prosthesis.

A system is disclosed that includes an orthopedic brace including a first member and a second member, wherein the first member is configured to control movement of a first component of an orthopedic joint prosthesis relative to the second member configured to control movement of a second component of the orthopedic joint prosthesis; one or more sensors configured to detect a change in an orientation of a subject's position in an environment and configured to detect one or more alignment orientations of the first component relative to the second component of the orthopedic joint prosthesis; one or more controllers in communication with the one or more sensors, wherein the one or more sensors are configured to report to the one or more controllers the one or more alignment orientations and the change in the orientation of the subject's position in the environment, and the one or more controllers are configured to control activity of the first member relative to the second member of the orthopedic brace, wherein the orthopedic brace is configured to adjust the one or more alignment orientations of the first component relative to the second component of the orthopedic joint prosthesis.

A method for preventing dislocation of an orthopedic joint prosthesis in a mammalian subject apparatus is disclosed that includes providing an orthopedic brace including a first member and a second member, wherein the first member is configured to control movement of a first component of an orthopedic joint prosthesis relative to the second member configured to control movement of a second component of the orthopedic joint prosthesis in the subject; detecting an orientation of the subject having the orthopedic joint prosthesis in an environment by one or more sensors in proximity to the subject; detecting one or more alignment orientations of the first component relative to the second component of the orthopedic joint prosthesis by the one or more sensors; communicating on the orientation of the subject and the one or more alignment orientations to one or more controllers; and adjusting an alignment of the first component relative to the second component of the orthopedic joint prosthesis in response to a signal from the one or more controllers to the first member and the second member of the orthopedic brace.

FIG. 1 is a schematic of a diagrammatic view of an apparatus including an orthopedic brace for an orthopedic joint prosthesis. The apparatus 100 comprises an orthopedic brace 110 including a first member 120 and a second member 130, wherein the first member is configured to control movement of a first component 180 of an orthopedic joint prosthesis 180, 190 relative to the second member configured to control movement of a second component 190 of the orthopedic joint prosthesis 180, 190. In an embodiment, the orthopedic brace 110 includes the first member 120 configured to be secured to the pelvic region and hip bone of the subject and includes the second member 130 configured to be secured to the leg region and/or femur of the subject. The orthopedic brace 110 may be external and strapped or attached surrounding the skin of the subject and configured to adjust the alignment of the orthopedic joint prosthesis. The orthopedic brace 110 may be fully or partially internal, for example, affixed to the bone of the subject and may have transcutaneous attachments to an external part of the brace and configured to adjust the alignment of the orthopedic joint prosthesis. The apparatus 100 includes one or more sensors 140 configured to be remote from the orthopedic joint prosthesis, wherein the one or more sensors 140 are configured to detect one or more alignment orientations of the first component 180 relative to the second component 190 of the orthopedic joint prosthesis 180, 190; and the one or more sensors 140 are configured to measure the one or more alignment orientations of the first component relative to the second component of the orthopedic joint prosthesis 180, 190. The apparatus 100 includes one or more controllers in communication with the one or more sensors 140, wherein the one or more sensors 140 report on the one or more alignment orientations to the one or more controllers 150, and the one or more controllers 150 are configured to control activity of the of the orthopedic brace 110, e.g., to control movement of the first member 120 relative to the second member 130 of the orthopedic brace 110, and wherein the orthopedic brace is configured to adjust the one or more alignment orientations of the first component relative to the second component of the orthopedic joint prosthesis 180, 190. The one or more sensors 140 may be remote from the orthopedic joint prosthesis 180, 190 and may be integrated or attached to the first member 120 and/or the second member 130 of the orthopedic brace 110. The apparatus 100 includes one or more force-applying elements 160 configured to control movement of the first member 120 relative to the second member 130, wherein the one or more force-applying elements 160 are configured to permit unrestrained motion of the orthopedic joint prosthesis 180, 190 under a first set of the one or more alignment orientations and are configured to permit restrained motion of the orthopedic joint prosthesis 180, 190 under a second set of the one or more alignment orientations. The one or more sensors may include, but are not limited to, ultrasound transducers, inertia-based sensors, or accelerometers.

Figure 2:
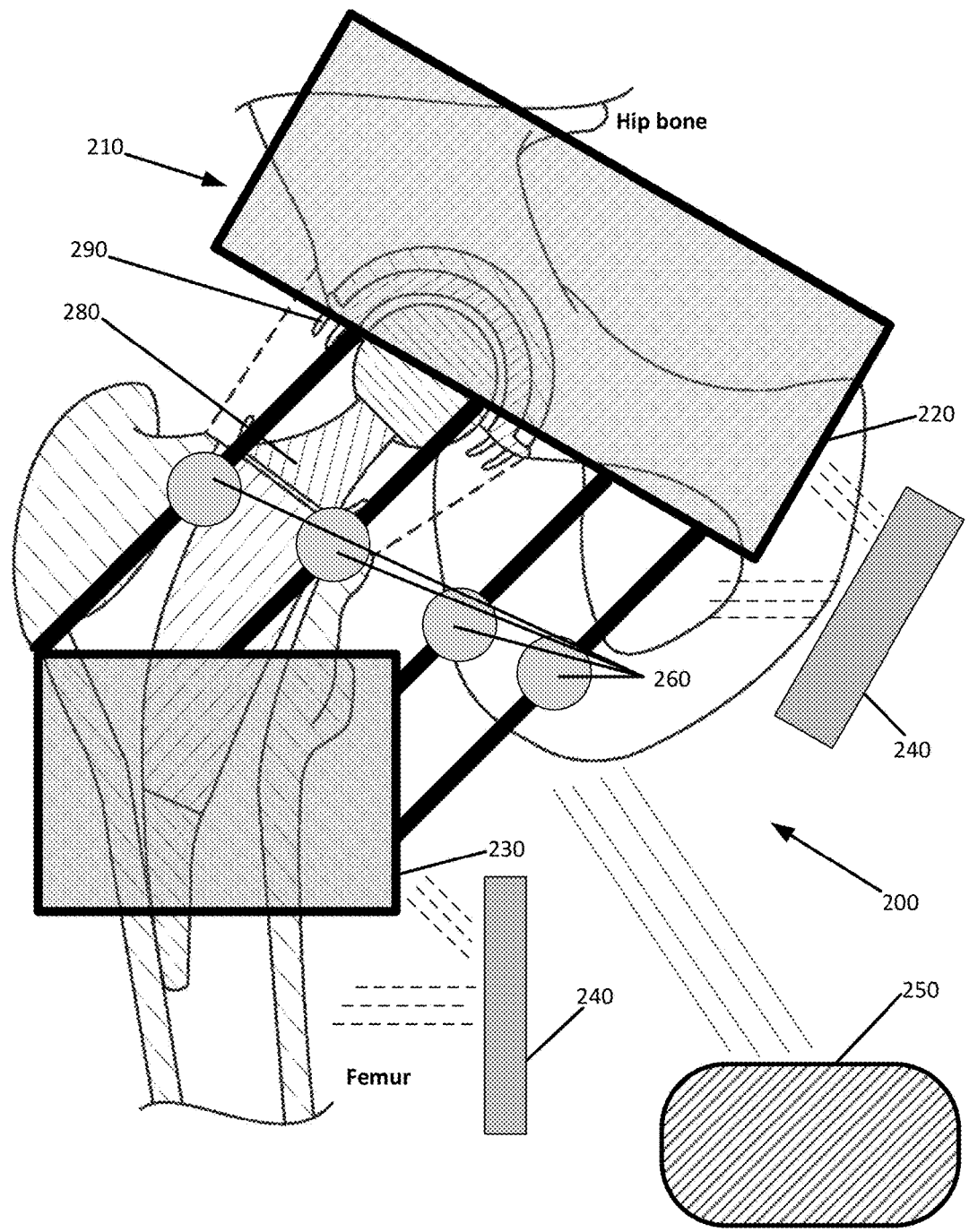
FIG. 2 is a schematic of a diagrammatic view of an apparatus including an orthopedic brace and one or more sensors configured to be remote from an orthopedic joint prosthesis.

FIG. 2 is a schematic of a diagrammatic view of an apparatus including an orthopedic brace for an orthopedic joint prosthesis. The apparatus 200 comprises an orthopedic brace 210 including a first member 220 and a second member 230, wherein the first member is configured to control movement of a first component 280 of an orthopedic joint prosthesis 280, 290 relative to the second member configured to control movement of a second component 290 of the orthopedic joint prosthesis 280, 290 and the one or more sensors are configured to measure the one or more alignment orientations of the first component relative to the second component of the orthopedic joint prosthesis. In an embodiment, the orthopedic brace 210 includes the first member 220 configured to be secured to the pelvic region and/or the hip bone of the subject and includes the second member 230 configured to be secured to the leg region and/or the femur of the subject. The apparatus 200 includes one or more sensors configured to be remote from the orthopedic joint prosthesis, wherein the one or more sensors 240 are configured to detect one or more alignment orientations of the first component 280 relative to the second component 290 of the orthopedic joint prosthesis 280, 290. The apparatus 200 includes one or more controllers 250 in communication with the one or more sensors 240, wherein the one or more sensors 240 report on the one or more alignment orientations to the one or more controllers 250, and the one or more controllers 250 are configured to control activity, e.g., to control movement, of the first member 220 relative to the second member 230 of the orthopedic brace 210, and wherein the orthopedic brace is configured to adjust the one or more alignment orientations of the first component relative to the second component of the orthopedic joint prosthesis. The one or more sensors 240 may be remote from the orthopedic joint prosthesis 280, 290 and may be separate or detached from the first member 220 and/or the second member 230 of the orthopedic brace 220. The apparatus 200 includes one or more force-applying elements 260 configured to control movement of the first member 220 relative to the second member 230, wherein the one or more force-applying elements 260 are configured to permit unrestrained motion of the orthopedic joint prosthesis 280, 290 under a first set of the one or more alignment orientations and are configured to permit restrained motion of the orthopedic joint prosthesis 280, 290 under a second set of the one or more alignment orientations.

Figure 3:
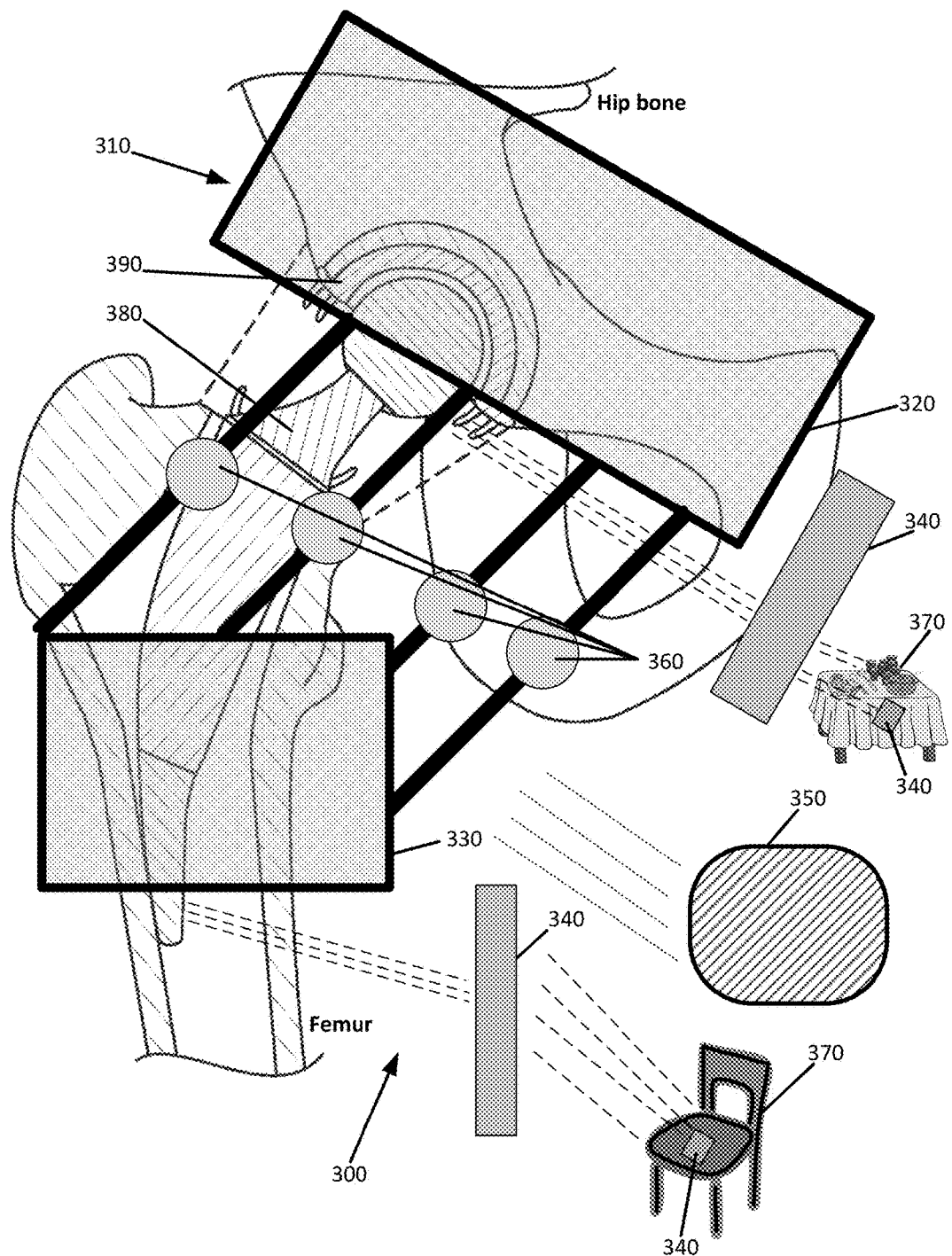
FIG. 3 is a schematic of a diagrammatic view of an apparatus including an orthopedic brace and one or more environmental sensors configured to detect a change in an orientation of an orthopedic joint prosthesis in the subject relative to the subject's position in an environment.
Figure 4:
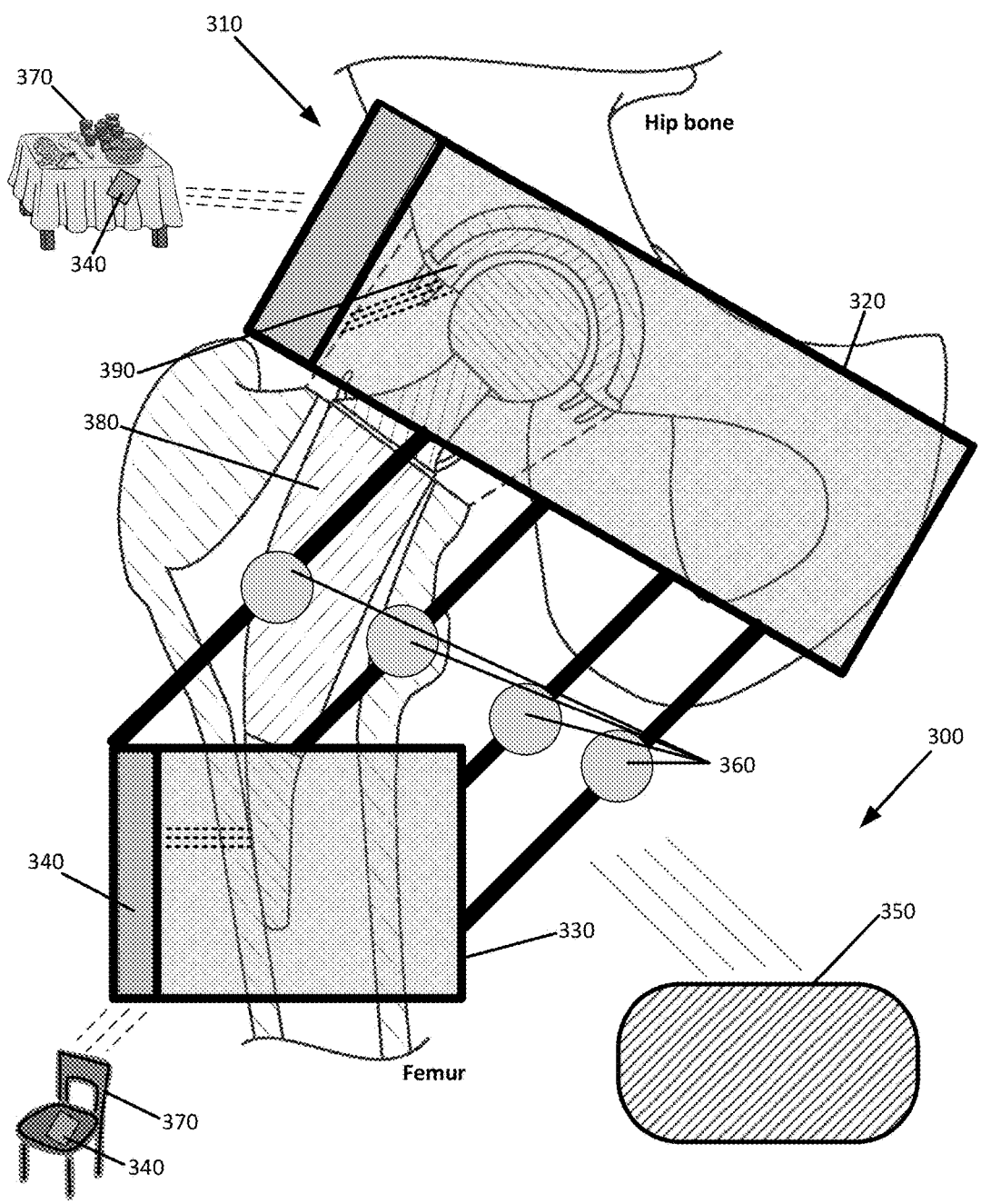
FIG. 4 is a schematic of a diagrammatic view of an apparatus including an orthopedic brace and one or more environmental sensors configured to detect a change in an orientation of an orthopedic joint prosthesis in the subject relative to the subject's position in an environment.

FIGS. 3 and 4 are schematics of a diagrammatic view of an apparatus including an orthopedic brace for an orthopedic joint prosthesis. The apparatus 300 comprises an orthopedic brace 310 including a first member 320 and a second member 330, wherein the first member 320 is configured to control movement of a first component 380 of an orthopedic joint prosthesis relative to the second member 330 configured to control movement of a second component 390 of the orthopedic joint prosthesis 380, 390. In an embodiment, the orthopedic brace 310 includes the first member 320 configured to be secured to the pelvic region and/or the hip bone of the subject and includes the second member 330 configured to be secured to the leg region and/or the femur of the subject. The orthopedic brace may be external to the limb of the subject or internal to the limb of the subject. The apparatus 300 includes one or more environmental sensors 340 configured to detect a change in an orientation of the orthopedic joint prosthesis 380, 390 in the subject relative to the subject's position in an environment or to an item associated with an environment 370, e.g., table, chair, wall of a room, or floor of a room. The one or more sensors 340 are configured to measure the one or more alignment orientations of the first component relative to the second component of the orthopedic joint prosthesis 380, 390. The apparatus 300 includes one or more controllers 350 in communication with the one or more environmental sensors 340, wherein the one or more environmental sensors 340 report on the one or more alignment orientations to the one or more controllers 350, and the one or more controllers 350 are configured to control activity, e.g., to control movement, of the first member 320 relative to the second member 330 of the orthopedic brace 310, and wherein the orthopedic brace is configured to adjust the one or more alignment orientations of the first component relative to the second component of the orthopedic joint prosthesis 380, 390. The environmental sensor may be configured to detect a change in an orientation of a subject's position in an environment and one or more alignment orientations of the first component relative to the second component of the orthopedic joint prosthesis. The one or more environmental sensors 340 may include imaging devices, e.g., cameras or scanners, placed in the subject's home at strategic locations to monitor the subject's movements and to monitor the hip joint alignment of the subject and to signal to the controller 350. The controller 350 may inform an actuator system associated with one or more force-applying elements 360 on the orthopedic brace 310 to actuate corrective alignment to the brace if misalignment or dangerous alignment is detected. In an embodiment, the one or more environmental sensors 340 may include sensors, e.g., force-sensitive resistors, accelerometers, gyroscopes, or electric field sensors, in the subject's shoes to detect unsafe movements of an artificial knee joint prosthesis and to detect imbalances that may lead to stumbles and/or falls. The apparatus 300 includes one or more force-applying elements 360 configured to control movement of the first member 320 relative to the second member 330. The one or more force-applying elements 360 of the orthopedic brace 310 may be configured to permit unrestrained motion of the orthopedic joint prosthesis 380, 390 under a first set of the one or more alignment orientations of the orthopedic joint prosthesis, and the orthopedic brace 310 is configured to permit restrained motion of the orthopedic joint prosthesis 380, 390 under a second set of the one or more alignment orientations of the orthopedic joint prosthesis. The one or more environmental sensors 340 may be configured to be remote from the orthopedic joint prosthesis 380, 390. In FIG. 3, the one or more environmental sensors 340 are remote from the first member 320 and the second member 330 of the orthopedic brace 310. In FIG. 4, the one or more environmental sensors 340 are in contact with the first member 320 and/or the second member 330 of the orthopedic brace 310. In FIGS. 3 and 4, in addition or alternatively, the one or more environmental sensors 340 may be on the wall or on furniture in the environment.

Figure 5:
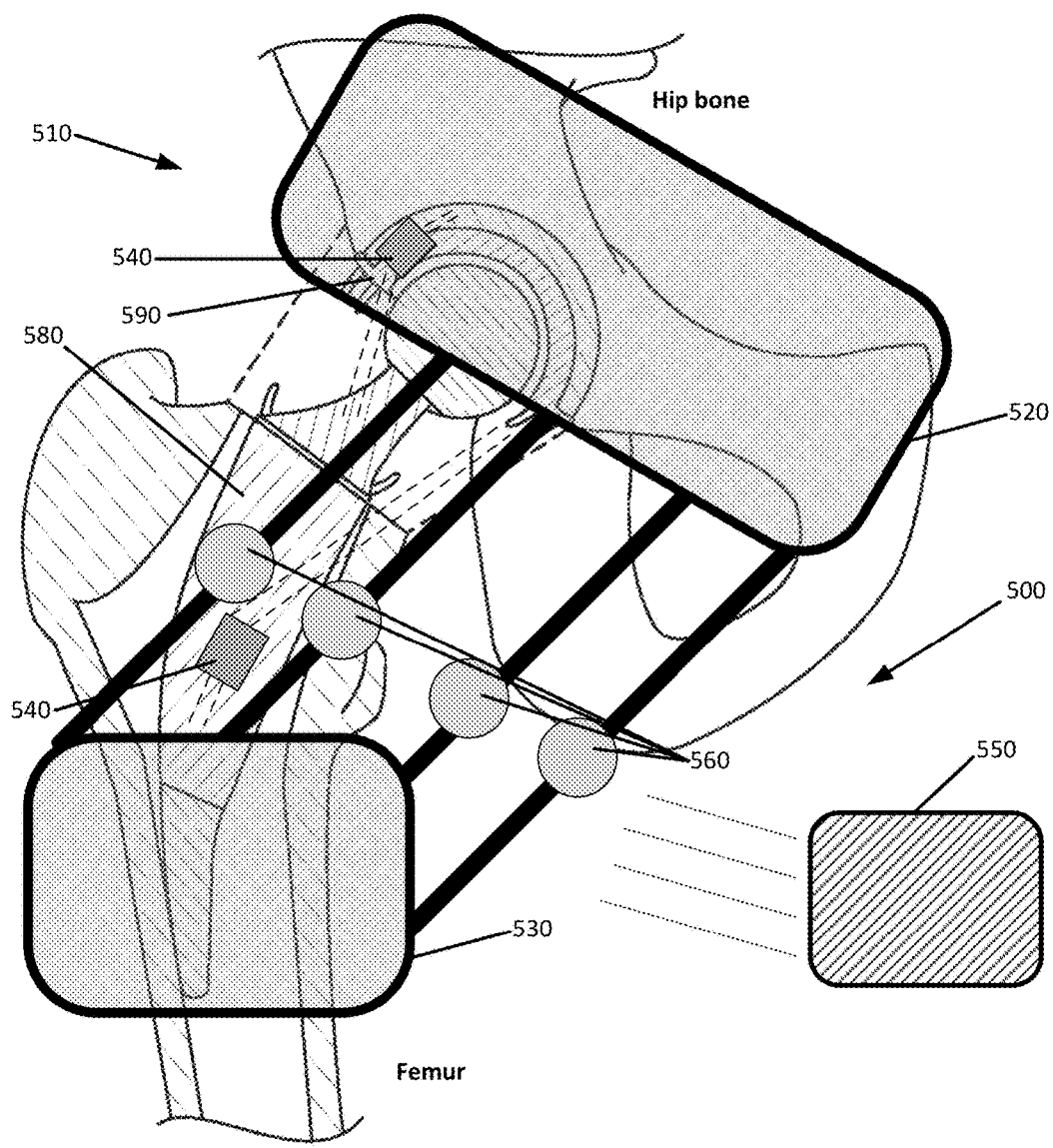
FIG. 5 is a schematic of a diagrammatic view of an apparatus including an orthopedic brace and one or more sensors configured to contact an orthopedic joint prosthesis.

FIG. 5 is a schematic of a diagrammatic view of an apparatus including an orthopedic brace for an orthopedic joint prosthesis. The apparatus 500 comprises an orthopedic brace 510 including a first member 520 and a second member 530 configured to control movement of a first component 580 of an orthopedic joint prosthesis 580, 590 relative to a second component 590 of the orthopedic joint prosthesis. In an embodiment, the orthopedic brace 510 includes the first member 520 configured to be secured to the pelvic region and/or the hip bone of the subject and includes the second member 530 configured to be secured to the leg region and/or the femur of the subject. The apparatus 500 includes one or more sensors 540 configured to contact the orthopedic joint prosthesis 580, 590, wherein the one or more sensors 540 are configured to detect one or more alignment orientations of the first component relative to the second component of the orthopedic joint prosthesis 580, 590. The apparatus 500 includes one or more controllers 550 in communication with the one or more sensors 540 wherein the one or more sensors 540 report on the one or more alignment orientations to the one or more controllers 550, and the one or more controllers 550 are configured to control activity. e.g., to control movement, of the first member 520 relative to the second member 530 of the orthopedic brace 510, and wherein the orthopedic brace is configured to adjust the one or more alignment orientations of the first component relative to the second component of the orthopedic joint prosthesis 580, 590. The orthopedic brace 510 includes one or more force-applying elements 560 configured to control movement of the first member 520 relative to the second member 530 of the orthopedic brace, wherein the one or more force-applying elements 560 in response to the one or more controllers 550 are configured to permit unrestrained motion of the orthopedic joint prosthesis under a first set of the one or more alignment orientations and are configured to permit restrained motion of the orthopedic joint prosthesis under a second set of the one or more alignment orientations.

Figure 6:
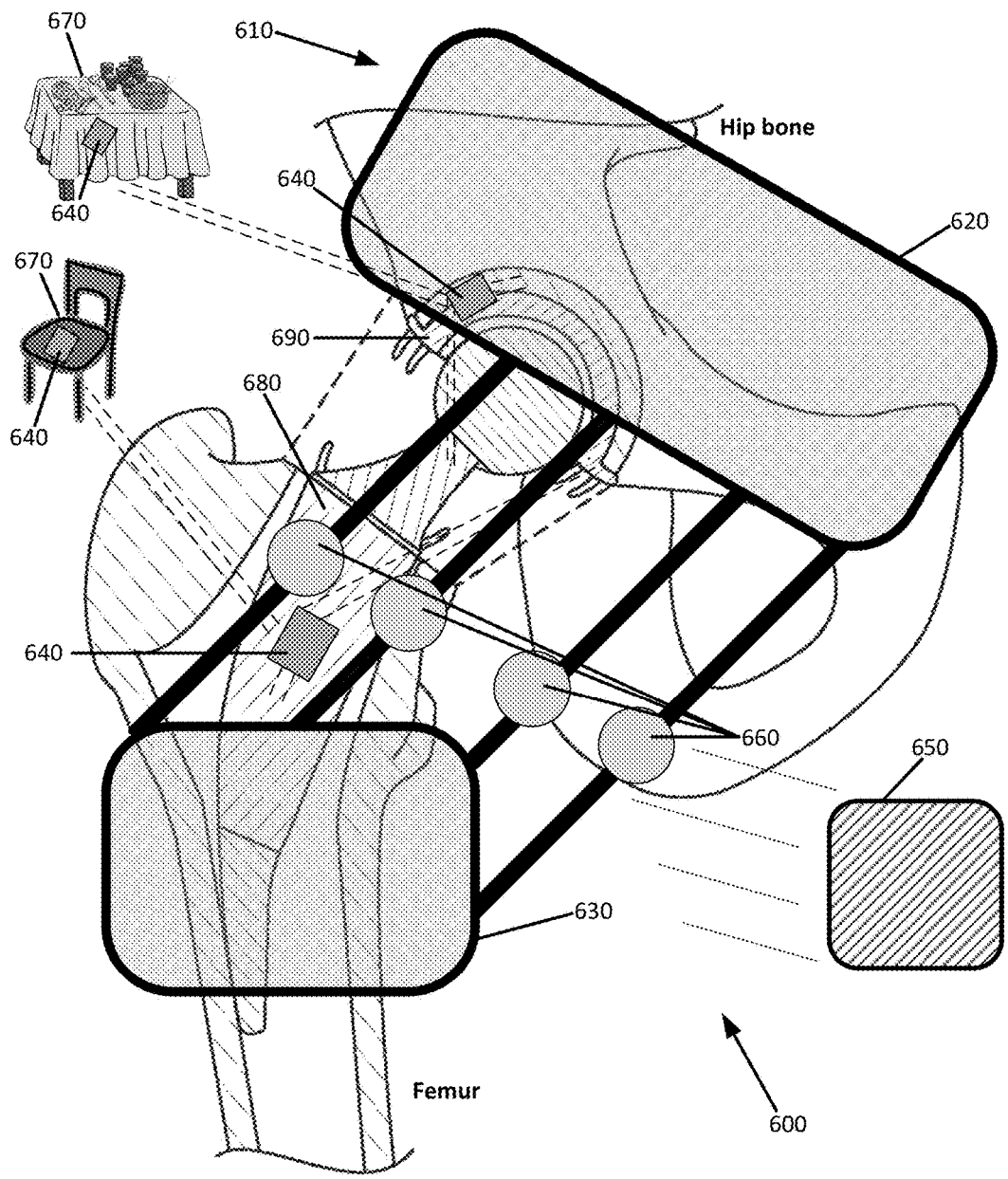
FIG. 6 is a schematic of a diagrammatic view of an apparatus including an orthopedic brace and one or more sensors configured to contact an orthopedic joint prosthesis.

FIG. 6 is a schematic of a diagrammatic view of an apparatus including an orthopedic brace for an orthopedic joint prosthesis. The apparatus 600 comprises an orthopedic brace 610 including a first member 620 and a second member 630 configured to control movement of a first component 680 of an orthopedic joint prosthesis relative to a second component 690 of the orthopedic joint prosthesis 680, 690. In an embodiment, the orthopedic brace 610 includes the first member 620 configured to be secured to the pelvic region and/or the hip bone of the subject and includes the second member 630 configured to be secured to the leg region and/or the femur of the subject. The apparatus 600 includes one or more sensors 640 configured to contact the orthopedic joint prosthesis 680, 690, wherein the one or more sensors 640 are configured to detect one or more alignment orientations of the first component relative to the second component of the orthopedic joint prosthesis 680, 690. The apparatus 600 includes one or more controllers 650 in communication with the one or more sensors 640, wherein the one or more sensors 640 report on the one or more alignment orientations to the one or more controllers 650, and the one or more controllers 650 are configured to control activity, e.g., to control movement, of the first member 620 relative to the second member 630 of the orthopedic brace 610, and wherein the orthopedic brace is configured to adjust the one or more alignment orientations of the first component relative to the second component of the orthopedic joint prosthesis 680, 690. The one or more sensors 640 may also include one or more environmental sensors 640 configured to detect a change in an orientation of the orthopedic joint prosthesis 680, 690 in the subject relative to the subject's position in an environment 670, or to an item associated with an environment, e.g., table, chair, wall of a room, or floor of a room. The one or more environmental sensors may be configured to be in contact with the orthopedic joint prosthesis and may interact via wireless communication with portions of the apparatus including the orthopedic brace, one or more force-applying elements, and/or the one or more controllers. Alternatively, the one or more environmental sensors 640 may be on the wall or on furniture in the environment. The orthopedic brace 610 includes one or more force-applying elements 660 configured to control movement of the first member 620 relative to the second member 630 of the orthopedic brace, wherein the one or more force-applying elements 660 in response to the one or more controllers 650 are configured to permit unrestrained motion of the orthopedic joint prosthesis under a first set of the one or more alignment orientations and are configured to permit restrained motion of the orthopedic joint prosthesis under a second set of the one or more alignment orientations. The apparatus may include wireless communication between portions of the apparatus including the orthopedic brace, one or more force-applying elements, one or more controllers, and one or more sensors. The apparatus may include wireless communication between portions of the apparatus, including, for example, body area network; personal area network; Bluetooth® short range wireless communication protocol, or radio communication technologies.

Figure 7:
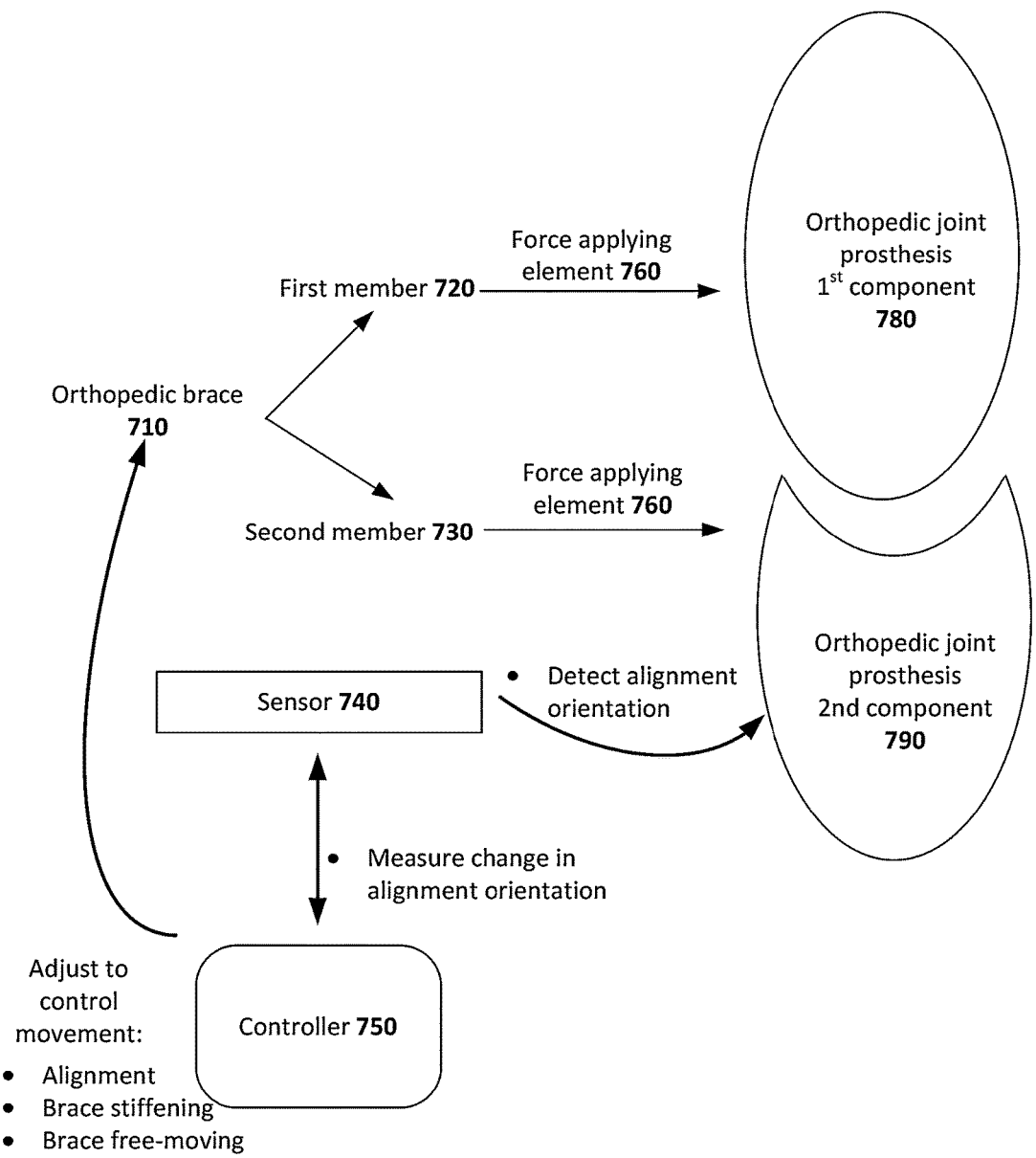
FIG. 7 is a schematic of a diagrammatic view of an apparatus including an orthopedic brace for an artificial orthopedic joint prosthesis.

FIG. 7 is a schematic of a diagrammatic view of an apparatus including an orthopedic brace for an orthopedic joint prosthesis. The apparatus 700 comprises an orthopedic brace 710 including a first member 720 and a second member 730, wherein the first member is configured to control movement of a first component 780 of an orthopedic joint prosthesis 780, 790 relative to the second member configured to control movement of a second component 790 of the orthopedic joint prosthesis 780, 790. In an embodiment, the orthopedic brace 710 includes the first member 720 configured to be secured to the pelvic region and/or hip bone of the subject and includes the second member 730 configured to be secured to the leg region and/or femur of the subject. The apparatus 700 includes one or more sensors 740 configured to detect one or more alignment orientations of the first component 780 relative to the second component 790 of the orthopedic joint prosthesis 780, 790. The apparatus 700 includes one or more controllers 750 in communication with the one or more sensors 740, wherein the one or more sensors 740 report on the one or more alignment orientations to the one or more controllers 750, and the one or more controllers 750 are configured to control activity, e.g., to control movement, of the first member 720 relative to the second member 730 of the orthopedic brace 710, and wherein the orthopedic brace is configured to adjust the one or more alignment orientations of the first component relative to the second component of the orthopedic joint prosthesis 780, 790. The orthopedic brace 710 in communication with the one or more controllers 750 is configured to adjust an alignment of the first component 780 relative to the second component 790 of the orthopedic joint prosthesis. In some embodiments, the one or more sensors 740 may be remote from the orthopedic joint prosthesis 780, 790 and/or may be integrated or attached to the first member 720 or the second member 730 of the orthopedic brace 710. The one or more sensors 740 may be in contact with the orthopedic joint prosthesis. The one or more sensors 740 may be one or more environmental sensors configured to detect an orientation of a subject's position in an environment and configured to detect one or more alignment orientations of the first component relative to the second component of the orthopedic joint prosthesis. The apparatus 700 includes one or more force-applying elements 760 configured to control movement of the first member 720 relative to the second member 730, wherein the one or more force-applying elements 760 are configured to permit unrestrained motion (brace free-moving) of the orthopedic joint prosthesis 780, 790 under a first set of the one or more alignment orientations and are configured to permit restrained motion (brace stiffening) of the orthopedic joint prosthesis 780, 790 under a second set of the one or more alignment orientations. In some embodiments, the first set of the one or more alignment orientations may include physiologically normal alignment of the orthopedic joint prosthesis, and the second set of the one or more alignment orientations includes physiologically abnormal alignment of the orthopedic joint prosthesis. The sensor 740 and the controller 750 may communicate in a closed loop. The controller controls the sensor which informs the controller, and the controller controls activity of the orthopedic brace 710. The controller may signal the sensor 740 and the sensor 740 may detect one or more conditions including, but not limited to, alignment, positioning, disposition, attitude, movement, friction or temperature of the orthopedic joint prosthesis, and inform the controller 750. The controller 750, based on the information from the sensor 740, may signal the sensor 740 to detect repeatedly or to detect further conditions. The controller 750, based on the information from the sensor 740, may also control the activity of the orthopedic brace 710 and may then control the sensor 740 to detect conditions, including those affected by the brace. The sensor 740 may sense one or more conditions of the brace or one or more conditions in the environment surrounding the subject. The one or more conditions include, but are not limited to, pressure, angle, motion, strain, flexion, extension, position, force, speed, or acceleration of the orthopedic joint prosthesis. The controller 750 in communication with the sensor 740 may control one or more of conditions. The controller 750 may control movement of the orthopedic brace by controlling a rate of movement, locking to prevent movement, or allowing the brace to move freely. The controller 750 may control scanning by the sensors of the orthopedic brace, the orthopedic joint prosthesis, or the environment surrounding the subject.

Figure 8:
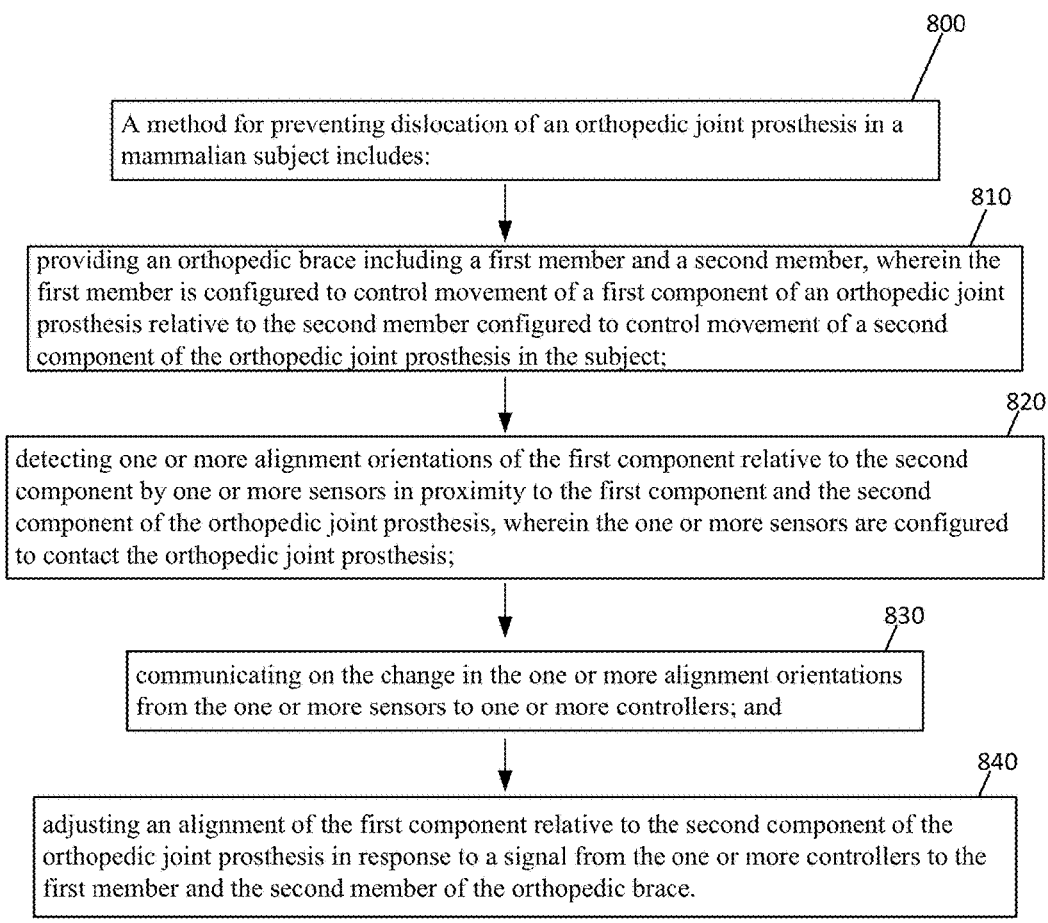
FIG. 8 is a schematic of a diagrammatic view of a method for preventing dislocation of an orthopedic joint prosthesis in a mammalian subject.

FIG. 8 is a schematic of a diagrammatic view of a method. A method for preventing dislocation of an orthopedic joint prosthesis in a mammalian subject 800 includes: providing an orthopedic brace 810 including a first member and a second member, wherein the first member is configured to control movement of a first component of an orthopedic joint prosthesis relative to the second member configured to control movement of a second component of the orthopedic joint prosthesis in the subject; detecting one or more alignment orientations 820 of the first component relative to the second component by one or more sensors in proximity to the first component and the second component of the orthopedic joint prosthesis, wherein the one or more sensors are configured to contact the orthopedic joint prosthesis; communicating on the one or more alignment orientations 830 from the one or more sensors to one or more controllers; and adjusting an alignment 840 of the first component relative to the second component of the orthopedic joint prosthesis by the orthopedic brace in response to a signal from the one or more controllers to the first member and the second member of the orthopedic brace.

Figure 9:
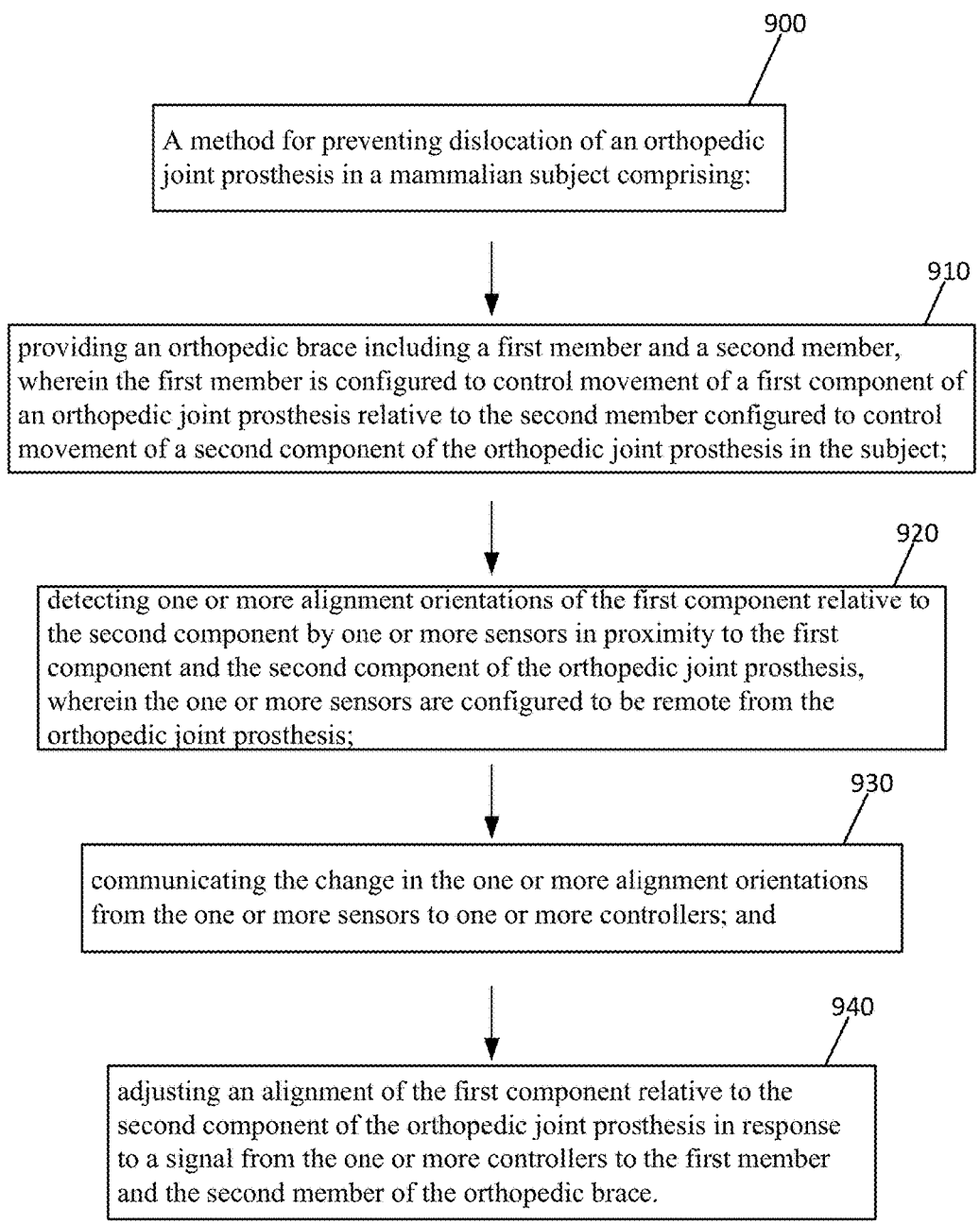
FIG. 9 is a schematic of a diagrammatic view of a method for preventing dislocation of an orthopedic joint prosthesis in a mammalian subject.

FIG. 9 is a schematic of a diagrammatic view of a method. A method for preventing dislocation of an orthopedic joint prosthesis in a mammalian subject 900 includes: providing an orthopedic brace 910 including a first member and a second member, wherein the first member is configured to control movement of a first component of an orthopedic joint prosthesis relative to the second member configured to control movement of a second component of the orthopedic joint prosthesis in the subject; detecting one or more alignment orientations 920 of the first component relative to the second component by one or more sensors in proximity to the first component and the second component of the orthopedic joint prosthesis, wherein the one or more sensors are configured to be remote from the orthopedic joint prosthesis; communicating on the one or more alignment orientations 930 from the one or more sensors to one or more controllers; and adjusting an alignment 940 of the first component relative to the second component of the orthopedic joint prosthesis by the orthopedic brace in response to a signal from the one or more controllers to the first member and the second member of the orthopedic brace.

FIG. 10 is a schematic of a diagrammatic view of a method. A method for preventing dislocation of an orthopedic joint prosthesis in a mammalian subject 1000 includes: providing an orthopedic brace including a first member and a second member 1010, wherein the first member is configured to control movement of a first component of an orthopedic joint prosthesis relative to the second member configured to control movement of a second component of the orthopedic joint prosthesis in the subject; detecting a change in an orientation of the subject having the orthopedic joint prosthesis 1020 relative to the subject's position in an environment by one or more environmental sensors in proximity to the subject; detecting one or more alignment orientations 1030 of the first component relative to the second component of the orthopedic joint prosthesis by the one or more environmental sensors; communicating the change in the orientation of the subject 1040 and the one or more alignment orientations to one or more controllers; and adjusting an alignment of the first component relative to the second component of the orthopedic joint prosthesis 1050 with the first member and the second member of the orthopedic brace in response to a signal from the one or more controllers.

Orthopedic Brace

An orthopedic brace may include a first member and a second member, wherein the first member is configured to control movement of a first component of an orthopedic joint prosthesis relative to the second member configured to control movement of a second component of the orthopedic joint prosthesis. The orthopedic brace including the first member and the second member may include a pelvic or hip-engaging unit that is formed to conform to the contours of a human hip. This hip-engaging unit can include multi-positional connections that can enable expansion, contraction, and rotation to permit a prefabrication of the hip-engaging unit and a subsequent adjustment to the particular anatomy of the patient. The hip-engaging unit can include first and second rigid outer hip-engaging members with a relatively flexible rear connector plate adjustably interconnecting the first and second hip-engaging members. A closure system can securely mount the hip-engaging unit on the patient. The connector plate can have a bridge member extending vertically upward and across a hip band member to not only stiffen the connector plate from relative rotational movement, but also to provide a handle to permit an orthotist, a therapist or family care provider to assist in training the patient in the use of the orthosis. In another embodiment, the orthopedic brace may include a knee-engaging unit, an ankle-engaging unit, an elbow-engaging unit, finger-engaging unit, or a wrist-engaging unit. The orthopedic brace may include portions that engage a body part near the prosthetic joint, e.g., a leg-engaging unit, an arm-engaging unit, a hand-engaging unit.

An orthopedic brace may include one or more force-applying elements configured to control movement of the first member relative to the second member. The force-applying element may be an adjustable hinge unit provided to enable a range of both flexion/extension and abduction/adduction movement of the orthopedic joint prosthesis. An adjustable linkage system can extend across an articulated joint, e.g., a hip joint, to permit a setting of a range of abduction that can vary with flexion. Flexion can be controlled with a variable setting hinge member. A link member that can be adjusted in length is pivotally affixed on either side of the articulated joint. The link member can be fixed at a location offset from a first rotational axis of the hinge member. The articulated joint has a second rotational axis which can be offset approximately 90° from the first rotational axis of the hinge members whereby movement about the first rotational axis will cause movement of the articulated joint about the second rotational axis. Since the hinge member is adjustable to control the range of flexion and extension and the link member is adjustable to control adduction and abduction, a controlled compound motion is afforded the patient. An alternative adjustable hinge unit can utilize a variable setting hinge member with a pivotal joint member connecting the hinge member to a bar that is attached to the appendant orthotic member. A follower roller and cam member can control the bar's movement in adduction and abduction as the hinge member permits the hip joint to flex and extend. See, e.g., U.S. Pat. No. 6,589,195, which is incorporated herein by reference.

The orthopedic brace may include a controller to control activity of the orthopedic brace. The controller may control activity of the orthopedic brace by controlling a rate of movement, locking to prevent movement, or allowing the brace to move freely. The controller may control scanning by the sensors of the orthopedic brace, the orthopedic joint prosthesis, or the environment surrounding the subject. The controller may include an actuator unit as part of the force-applying element to apply force to an orthopedic joint prosthesis of the mammalian subject. The controller in communication with the sensor may determine an alignment orientation of the orthopedic joint prosthesis. The actuator unit is activated in response to a signal from the controller to correct the alignment orientation. In an embodiment, a method for preventing dislocation of an orthopedic joint prosthesis in a mammalian subject includes detecting one or more alignment orientations of the first component relative to the second component by one or more sensors in proximity to the first component and the second component of the orthopedic joint prosthesis and applying resistive force from the actuator unit of the force-applying element. The actuator unit in communication with the controller can modify the resistive force characteristics of the force-applying element by the controller and in response to the history of joint movement and utilizing data of joint modeling and movement modeling. The controller may process data based on current joint movement and based on historical joint movement of the subject in addition to data from joint three dimensional modeling and movement modeling. Based on data from the sensors and other processed data, the controller may determine a corrected position for the joint prosthesis and provide instructions for movement of the orthopedic brace to obtain the corrected position for the joint prosthesis.

The orthopedic brace including one or more force-applying elements may provide an alternative load path from, for example, the upper leg to the pelvis. Loads are normally transmitted from the upper leg through the pelvic joint to the pelvis. Force-applying elements incorporated with the orthopedic brace provide an alternate path for loads to be transmitted between muscles of the upper leg and muscles of the pelvis, with these loads bypassing the pelvic joint. In some embodiments, the force-applying elements are adjusted to provide more damping force (and therefore increased load bypassing of the pelvic joint) during flexion of the pelvic joint, such as when a person squats, as when a person goes down a stairway, or as when a person riding in a vehicle such as a boat has the floor of that vehicle suddenly rise toward the person.

The orthopedic brace may be configured to permit unrestrained motion of the orthopedic joint prosthesis under a first set of the one or more alignment orientations, and to permit restrained motion of the orthopedic joint prosthesis under a second set of the one or more alignment orientations. In some embodiments, the force-applying elements have a one or more adjustments that can provide a smaller damping force during extension of the pelvic joint. By having force-applying elements that provide less resistance to extension than to flexion, it is easier for a person to walk and more freely extend their leg (when the pelvic joint is generally unloaded), yet have the pelvis support apparatus provide a bypass path for loads during flexion (when the pelvic joint may be supporting some or all of the person's weight).

In other embodiments, the force-applying elements may provide extension forces greater than flexion forces. Such embodiments may be useful for exercising a pelvic joint, especially when the person is seated in a chair.

In addition to altering the load path from the upper leg to the pelvis, the force-applying elements may incorporate a damper to provide a means for dissipating the load being bypassed as the addition of heat to the damping fluid. The combination of lower loads on the pelvic joint and dissipation of some of the loads provides a general decrease in the fatigue level of the pelvic joint, allowing the user to perform at a higher level for a longer period of time.

In some embodiments, force-applying elements interconnect the upper leg and pelvis attachments. This force-applying elements may include a damper mechanism that provides a force which opposes flexion of the joint, extension of the joint, or both flexion and extension. In some embodiments this opposing force is a function of the angular velocity of the upper leg attachment relative to the pelvis attachment of the orthopedic brace. In other embodiments the opposing force is also, or alternatively, a function of the angular displacement of the upper leg attachment relative to the pelvis attachment of the orthopedic brace. In other embodiments the opposing force is also, or alternatively, a function of the history of the angular velocity and/or the angular position of the upper leg attachment relative to the pelvis attachment of the orthopedic brace.

In some embodiments, the force-applying elements may include one or more fluid dampers, such as a hydraulic damper or pneumatic damper. In an embodiment, the force-applying elements include one or more hydraulic shock absorbers whose resistance is a function of direction, velocity, and manual adjustment setting. In some embodiments, the fluid damper is a linear device, such as with a piston and rod that extend out from a cylinder. In other embodiments, the fluid damper is of the rotary type. See, e.g., U.S. Pat. No. 7,048,098 to Moradian, and U.S. Patent Application Publication No. 2006/0096818 A1 (to Moradian), which are incorporated herein by reference.

In some embodiments, the orthopedic brace including a first member and a second member includes upper leg and pelvis attachments interconnected by interior and exterior joint assemblies. Each of the attachment assemblies of the orthopedic brace are adapted and configured to permit less than full flexion of a pelvic joint. In an embodiment, the attachment assembly includes impact-resistant covers for the front side of the upper leg and the front side of the pelvis, as well as a cover for the front of the pelvic joint.

In some embodiments, the orthopedic brace includes an electronic data logger. The data logger records electrical signals which are related to the load being transmitted by the force-applying elements, the angular position of the upper leg attachment relative to the pelvis attachment, and/or the angular velocity of the upper leg attachment relative to the pelvis attachment. See, e.g., U.S. Pat. No. 7,507,215, which is incorporated herein by reference.

Force-Applying Elements and Members for an Orthopedic Brace

An orthopedic brace including force-applying elements is provided for applying an adjustable therapeutic amount of force to an orthopedic joint prosthesis. Sensors in combination with controllers may be used to detect the amount of force applied and to provide an indication to the user of the amount of force applied. Numerous features may be used in various configurations for a variety of orthopedic braces, including, but not limited to, hip braces, knee braces, elbow braces, shoulder braces, torso braces, wrist braces, finger braces, ankle braces, or any orthotic device for which it is desirable to apply a controlled amount of force to effect a therapeutic benefit to the orthopedic joint prosthesis. In some embodiments, the force is drawn across an orthopedic joint prosthesis of the subject.

The apparatus includes the controller for controlling forces applied by force-applying elements of an orthopedic brace. In some embodiments, the apparatus includes a force dosimeter mounted to the orthopedic brace or to the orthopedic joint prosthesis and operably connected to force-applying elements to apply an adjustable amount of force to at least one point on the orthopedic brace and force to the orthopedic joint prosthesis. A force sensor mounted to the orthopedic brace or to the orthopedic joint prosthesis is operably configured to detect the amount of force applied. An indicator mounted to the orthopedic brace or remote from the orthopedic brace is operably configured with the force sensor to indicate the amount of force applied.

In some embodiments, the force sensor is configured with a transducer that converts the detected amount of force into an electrical signal. The transducer may be in communication with a controller configured with instructions to control the indication provided by the indicator. The controller may be further configured with a memory and with instructions to store data pertaining to the amount of force applied at a given time when the apparatus including the orthopedic brace is in use by a subject. In some embodiments, the controller is further configured with a data communication device for communicating data regarding the applied force in real time to an external device or computing device, or data stored in the memory to an external device or computing device. In some embodiments, the data communication device uses a wireless communication protocol, such as a BlueTooth® wireless communication protocol.

The apparatus includes one or more sensors including contact sensors, e.g., proximity sensors. Proximity sensors for sensing an environment may include a flexible or stretchable substrate, one or more flexible or stretchable light emitting diode (LED) arrays supported by the substrate, one or more flexible or stretchable photodetector (PD) arrays supported by the substrate, and one or more barrier layers at least partially encapsulating the one or more LED arrays, at least part of the one or more PD arrays, or at least parts of both. In some embodiments, the one or more LED arrays comprise a large area array. The flexible or stretchable inorganic LED may have an average thickness less than or equal to 100 μm. In some embodiments, the one or more PD arrays comprise a large area array. The flexible or stretchable PD array may include one or more inorganic semiconductor elements having an average thickness less than or equal to 100 μm. one or more barrier layers at least partially encapsulating the one or more flexible or stretchable LED arrays and the one or more flexible or stretchable PD arrays, wherein the barrier layer prevents water from a biological environment from contacting at least a portion of the inorganic LEDs. In further embodiments, the apparatus including the one or more proximity sensors may further include a controller in electrical communication with the one or more LED arrays and/or PD arrays. Optionally, the one or more LED arrays and the one or more PD arrays are provided in one or more individually encapsulated layers in a multilayer stacked geometry. See, e.g., U.S. Patent Application Publication No. 2012/0165759, which is incorporated herein by reference. In an embodiment, the apparatus including the one or more proximity sensors is configured to operate in an in vivo biological environment. The apparatus including the proximity sensors may be used for sensing or actuating the tissue. The apparatus including the proximity sensors establishes conformal contact with the tissue in a biological environment. The biological environment may include, but is not limited to, heart tissue, brain tissue, skin, muscle tissue, nervous system tissue, vascular tissue, epithelial tissue, retina tissue, ear drum, tumor tissue, or digestive system. See, e.g., U.S. Patent Application Publication No. 2012/0157804, which is incorporated herein by reference.

In an embodiment, the force-applying elements of orthopedic brace include a mounting and a bracing member. The mounting is conformed to fit the orthopedic brace to a limb including an orthopedic joint prosthesis of a subject. The bracing member is engaged with the mounting to position the bracing member in a therapeutic position with respect to an orthopedic joint prosthesis of the subject. The bracing member of the force-applying element in combination with the sensor and controller include a force dosing device and a tensioning device engaged with the mounting, and connected to the bracing member at a first end and connected to force-applying element at a second end. The force dosing device is operably connected to the tensioning device to adjust an amount of force applied to the bracing member through the force-applying elements. A force sensor is mounted between the tensioning device and the mounting to detect the amount of force applied. The device further includes an indicator mounted on the mounting and operably connected to the force sensor to display an indication of the amount of force applied.

In some embodiments, the force-applying elements can be selected from the group consisting of a cable, a strap and a net. In certain embodiments, the force-applying elements may be a single cable. In other embodiments, the force-applying elements include a plurality of cables attached to the bracing member at a plurality of positions on the bracing member. In some embodiments, the force applied by the tensioning device is simultaneously applied to the plurality of cables when the force is adjusted with the dosimeter. In a particular embodiment, at least two of the plurality of cables attached to the bracing member at a plurality of positions form an "X" pattern on a lateral side of the device opposite the bracing member. The vertex of the X is positionable parallel to or colinear with an axis of rotation of the subjects joint.

In some embodiments, the tensioning device comprises at least one torsion spring attached to the force-applying elements. In embodiments that use a plurality of cables as force-applying elements, the tensioning device includes a plurality of torsion springs independently attached to the plurality of cables where each torsion spring is simultaneously adjustable by the force dosimeter.

The force dosimeter may include a ratchet assembly that engages the tensioning device in a first position to incrementally increase the amount of force applied, and which engages the tensioning device in a second position to decrease the amount of force applied.

The mounting for the brace apparatus may be formed as a fabric sleeve having an inner and outer surface. The force-applying elements includes at least one cable that runs in contact with a portion of the outer surface of the sleeve between the tensioning device and the point of contact on the bracing member. In some embodiments, the sleeve further includes a padded surface on the portion of the outer surface over which the cable is in contact. The sleeve may be further configured with an exterior sleeve cover that covers the portion of the outer surface over which the cable is in contact. In some embodiments, the fabric sleeve includes a pocket configured to removably hold the bracing member in at least one of a medial or lateral position with respect to a joint on the limb when the sleeve is worn by the subject.

In some embodiments, the force sensor may comprise a fluid filled bladder positioned between the tensioning device and mounting. The force sensor may include a pressure transducer configured to detect pressure in the bladder when force is applied by the force dosimeter and to convert the detected pressure into an electrical signal. Typically, the fluid is a gas and the force transducer is in fluid communication with the gas in the bladder through a tube. The bladder may include a gas impermeable sheath and may include a compressible foam insert within the sheath. See, e.g., U.S. Patent Application Publication No. 2006/0200057, which is incorporated herein by reference.

The orthopedic brace may include an actuator system to apply force to the orthopedic joint prosthesis. The actuator system may include one or more of electromechanical actuators, electrohydraulic actuators, linear hydraulic actuators, or rotational hydraulic actuators. The actuator system may be controlled by a microprocessor controller attached to and in communication with the orthopedic brace. The electromechanical actuator system of the orthopedic brace for extending and flexing a prosthetic joint of a subject may include a multi-motor assembly for providing a rotational output, a rotary-to-linear mechanism for converting the rotational output from the multi-motor assembly into a linear motion that ultimately extends and flexes the brace to manipulate the prosthetic joint, and a controller for operating the actuator system in several operational modes. The multi-motor assembly may combine power from two different sources, such that the multi-motor assembly can supply larger forces at slower speeds and smaller forces at higher speeds. The actuator may be specifically designed for extending and flexing the prosthetic joint of the subject, such as a hip, an ankle, a knee, an elbow, or a shoulder. The actuator system may be used to move any suitable object through any suitable movement (linear, rotational, or otherwise). See e.g., U.S. Pat. No. 8,058,823 issued to Horst et al. on Nov. 15, 2011 which is incorporated herein by reference.

The actuators may be constructed from titanium and attached to the pelvic and thigh members of the orthopedic brace to exert a linear force across a prosthetic hip joint to influence abduction/adduction and flexion/extension of the prosthetic hip joint prosthesis. Actuators may also exert rotational forces on the brace through a hinge incorporated in the orthopedic brace. See e.g., U.S. Pat. No. 5,421,810 issued to Davis et al. on Jun. 6, 1995 which is incorporated herein by reference.

Orthopedic Brace to Adjust Alignment Orientation of an Orthopedic Joint Prosthesis In some embodiments to overcome limitations in stride length and gait speed of the subject, the orthopedic brace including one or more force-applying elements may include a variable constraint hip mechanism to maintain posture while allowing for uninhibited sagittal hip movement. The objective of the variable constraint hip mechanism is to provide good hip and trunk stability and erect posture without interfering with functional lower-limb dynamic movements during walking and stair-climbing. The orthopedic brace, e.g., a trunk-hip-knee-ankle-foot orthosis is coupled to the body by means of chest, pelvic, and below-the-knee straps.

The force-applying element including the variable constraint hip mechanism may be configured to permit unrestrained motion of the orthopedic joint prosthesis under a first set of the one or more alignment orientations. The force-applying element including the variable constraint hip mechanism may be configured to permit restrained motion of the orthopedic joint prosthesis under a second set of the one or more alignment orientations. The force-applying element including the variable constraint hip mechanism includes a hydraulic system with double-acting cylinders linked to each of the first member and the second member of the orthopedic brace. The corresponding ports of the opposing cylinders are connected to produce a closed hydraulic circuit. Normally open two-way, two-position solenoid valves are attached to each port of the cylinders. Two additional normally closed two-way, two-position solenoid valves modulate the flow of fluid between the cap and rod ends of the hydraulic circuit and into an accumulator. Each hydraulic cylinder is mechanically linked to each of the first member and the second member via a custom rack-and-pinion transmission. When all the valves are de-energized, the mechanism provides the 1:1 hip coupling of a standard reciprocal gate orthosis. When one piston of a cylinder is forced to extend, the rod end of the piston of the contralateral cylinder is pressurized and thus forced to retract. By energizing specific solenoid valves, the first member and the second member of the orthopedic brace can be reciprocally coupled, unlocked to move freely, and independently locked against flexion or extension or both.

Each hydraulic rotary actuator of the variable constraint hip mechanism of the orthopedic brace is configured as follows. The cylinder is mounted to the thigh upright of the knee-ankle-foot orthosis via a clevis, and the pinion is fixed rigidly to the corset. The rack is connected to the rod via a clevis and meshed to the pinion, posterior relative to the hip joint. A polypropylene shield is placed around the pinion to protect the user from the gear teeth. The clevis connections made between the cylinder and thigh upright and between the cylinder rod and the rack allow the rotary actuator to move into abduction during donning and doffing. For real-time control, a slide potentiometer (Alps Electric Co; Tokyo, Japan) is instrumented to the rack to measure cylinder piston movement and digital pressure sensors (Gems Sensors Inc.; Plainville, Conn.) are attached at each port of the cylinder to monitor pressure. In addition, potentiometers are placed at the knee and ankle to measure angles and force-sensing resistors (FSRs) (B&L Engineering; Tustin, Calif.) are placed in the insoles to measure foot-to-floor contact.

The orthopedic brace may include a solenoid-actuated wrap-spring clutch mechanism employed for supporting the joint, including the knee or hip of the subject. The wrap-spring clutch knee mechanism may be installed at the knee joints of the orthopedic brace with a posterior offset to reduce knee flexion moment induced by gravity. A power source including a 5.9 W, 12 Vdc latching solenoid (Guardian Electric; Woodstock, Ill.) is used to engage/disengage the wrap-spring clutch (Warner Electric; South Beloit, Ill.). Unlatching (extension of the plunger out of the solenoid) disengages the clutch, which locks the knee against flexion but still allows extension. Latching (retraction of the plunger into the solenoid) engages the clutch, allowing for both knee flexion and extension. A pulse of 100 ms is used to latch/unlatch the latching solenoid. An optical switch (TT Electronics; Weybridge, United Kingdom) monitors the movement of the plunger of each latching solenoid to assure that the state transition (lock/unlock) of the knee has been completed. See, e.g., Kobetic et al., *J. Rehabilitation Research and Development* 46: 447-462, 2009, which is incorporated herein by reference.

Orthopedic Brace Including Sensors Contacting an Orthopedic Joint Prosthesis or Surrounding Tissue An orthopedic brace including one or more sensors may include one or more sensor affixed or attached onto or embedded into an orthopedic joint prosthesis. The one or more sensors may include, for example, proximity sensors, e.g., able to detect the proximity between portions of two or more components of the joint prosthesis, with changes in such proximity indicating movement. The one or more sensors may include, for example, location sensors attached onto or embedded into the joint prosthesis. Sensors may utilize, for example, electric, magnetic, optical, or sound technology, and may include one or more transducer. In an embodiment, an apparatus may include inductive sensors attached to or embedded into an orthopedic joint prosthesis or into the tissue surrounding the orthopedic joint prosthesis. See e.g., U.S. Pat. No. 6,245,109, which is incorporated herein by reference. Implanted strain sensors with micro-batteries may be used to monitor strain in soft, peri-articular tissues and communicate with a controller. See e.g., U.S. Pat. No. 4,813,435, which is incorporated herein by reference.

Orthopedic Brace Including Sensors and Controllers Utilizing Three Dimensional Modeling of Bone Joints Including Bone and Soft Tissue The apparatus including the orthopedic brace with the sensors and controllers may use a patient-specific three dimensional (3D) computer-generated model of a patient's joint. The patient-specific 3D computer-generated model may include modeling of bone and soft tissue in combination with modeling of the orthopedic joint prosthesis. The model is then registered to the patient's actual bone.

Sensors in communication with controllers associated with the orthopedic brace are configured so that the orthopedic brace permits unrestrained motion of the hip joint prosthesis under a first set of alignment orientations and permits restrained motion of the hip joint prosthesis under a second set of alignment orientations. Ultrasound sensors are attached to the external hip joint brace to detect the alignment and orientation of the hip joint prosthesis and to signal the controller with data regarding alignment of the first component relative to the second component of the hip joint prosthesis. The controller may use data from the ultrasound sensors in combination with patient-specific 3D models of the bones and joints to control motion of the orthopedic brace. To evaluate knee kinematics, patient-specific 3D models of the distal femur, proximal tibia, and the patella are constructed using pulse echo A-mode ultrasound based 3D model reconstruction technology. In addition, patient-specific kinematic data is obtained for the motions of the femur, tibia, and patella using pulse A-mode ultrasound. Finally, patient-specific vibration data is obtained while the knee joint is taken through a range of motion and loaded in real-world conditions. The vibration data and kinematic data may be taken at the same time using the single data acquisition device.

In an embodiment, patient-specific 3D models may be obtained using ultrasound-based joint kinematics tracking with or without vibration detection. See e.g., U.S. Patent Application Publication No. 2010/0198067, which is incorporated herein by reference. Information for the 3D models can be obtained prior to use of the orthopedic brace and stored in and utilized by the one or more controllers. 3D models may be obtained or optimized using ultrasound sensors associated with the orthopedic brace. The sensors, e.g., sensors remote from the orthopedic joint prosthesis and/or sensors attached to the orthopedic joint prosthesis, interacts in real time with these other modules providing dynamic force data. Additional sensors may be remote from and/or attached to the hip, upper leg, lower leg, or foot of the subject to gather kinematic data.

The pulse echo A-mode ultrasound based 3D model reconstruction module constructs a 3D model of a mammalian subject's bones by transcutaneously acquiring a set of 3D data points that in total are representative of the shape of the bone's surface using a tracked pulse echo A-mode ultrasound probe. The probe may consist of a single ultrasound transducer attached to a global localizer. The global localizer may be optical, inertial, electromagnetic or ultra wide band radio frequency. The probe may be battery-powered and connected wirelessly to a computer or directly to the controller in order to record the set points and construct a unique or patient-specific bone model using an atlas-based deformable model technique.

The computer and/or the controller may include software that interprets data from the tracked pulse echo A-mode ultrasound probe and is operative to construct the 3D models of the patient's bones. The patient-specific bone is reconstructed using the set of points collected from the bone's surface transcutaneously by the tracked ultrasound probe. These points are then used by the atlas-based deformable model software to reconstruct the 3D model of the patient's bone.

In some embodiments, the software includes a plurality of bone models of the femur, tibia, and patella that are classified, for example, based upon ethnicity, gender, skeletal bone to be modeled, and the side of the body the bone is located. Each of these classifications is accounted for by the dropdown menus of the software so that the model initially chosen by the software most closely approximates the body and bone structure of the patient.

After the software selects the bone model to approximate the bone of the patient, the ultrasound transducer probe is repositioned on the exterior of the skin and data points are generated and applied to the model bone (in this case a distal femur), numerically recorded and viewable in a data window, and ultimately utilized by the software to conform the bone model to the subject's actual bone shape. A higher number of data points imposed on the model will generally result in a more accurate patient model. Nevertheless, in view of the model bones already taking into account numerous traits of the subject (ethnicity, gender, bone modeled, and body side of the bone), it is possible to construct an accurate subject-specific 3D model with as few as 150 data points, which typically can be taken by repositioning the probe over the bone for 30 seconds for each bone. In some embodiments, it is preferable for the data to be acquired both while the pelvic joint is bent and extended to more accurately shape the ends of the bones. This same procedure is repeated for the remaining bones of the joint, in this case the proximal end of the tibia and the femur, in order for the software to combine the bones thereby forming the joint. Ultrasound will not be affected whether the patient has a normal or prosthetic joint. The 3D model of the femur can be resected and attached with the implanted CAD model. See e.g., U.S. Patent Application Publication No. 2010/0198067, which is incorporated herein by reference.

Orthopedic Brace Including Sensor and Controller that Senses and Controls Alignment and Motion of Bone Joint and Bone Joint Prosthesis The orthopedic brace includes sensors that are in communication with controllers, wherein the sensors report on alignment orientations to the controllers. The sensors provide data with regard to tracking position and motion of bone joint and bone joint prosthesis. In an embodiment, the orthopedic brace may include contact sensors or remote sensors, e.g., pulse echo A-mode ultrasound transducers, to transcutaneously localize points on the bones surface. Commercially available transducers for use with the exemplary embodiments include, without limitation, the Olympus immersion unfocused 3.5 MHz transducer. In conjunction with the ultrasound transducers, a force-sensing shoe may detect the ground reactive pressures simultaneous with pelvic joint kinematic data acquisition.

Each ultrasound transducer is tracked using an accelerometer or a sensor-specific localizer, or any other appropriate inertial sensor. The resulting localized bone points generated from the outputs of the ultrasound transducers are used in combination with the patient specific 3D bone models to discern bone movement while the knee joint in motion. In some embodiments, remote sensors, e.g., ultrasound transducers, on the orthopedic brace and the foot force-sensing shoe are used to track pelvic joint kinematics and dynamic forces: (a) a sensor on a first member of the orthopedic brace is positioned proximate the distal portion of the pelvis; and (b) a sensor on a second member of the orthopedic brace is positioned proximate the distal end of the femur.

An orthopedic brace including one or more sensors includes a plurality of pulse echo A-mode ultrasound transducers for transcutaneous detection of the bone's surface and inertia-based localizers to track the motion of the ultrasound transducers, which in turn, track the motion of the bone. The orthopedic brace including one or more sensors may include a rigid or semi-rigid body having a plurality (two or more) of complementary metal oxide semiconductor inertia-based sensors attached thereto. The orthopedic brace including one or more sensors may include an accelerometer-based localizer to track each pulse echo A-mode ultrasound transducer mounted to the orthopedic brace. The localizer comprises a plurality of nodes, with each node comprising a CMOS accelerometer and a temperature sensor for thermal drift comparison. Each node is integrated to minimize noise and distortion. See e.g., U.S. Patent Application Publication No. 2010/0198067, which is incorporated herein by reference.

Orthopedic Brace Including Ultrasound Sensors and Transducers

An orthopedic brace including one or more sensors may include a plurality of transducers mounted to the orthopedic brace, to a limb of the subject, or to the orthopedic joint prosthesis. Each sensor and transducer is responsible for determining the location of a point on the surface of the bone for each motion tracking frame. Problems of locating and tracking the bone using ultrasound data are reduced as the motion of the bone relative to the skin is small compared to the gross joint motion. There are at least three approaches for tracking the motion of the ultrasound transducers themselves. The first approach, referred to as the Individual Transducer Tracking (ITT) approach, involves each transducer in the brace having an inertia-based localizer to individually track each transducer. Using the ITT approach, in exemplary form, the transducers are held together flexible length straps.

A second approach, referred to as the Inter-transducers Mechanical Links (ITML) approach, involves the transducers being connected to each other by movable mechanical links. Each mechanical link includes length and angle sensors that allow for detection of the movement of the transducers relative to one another and the relative translational motions of the links. Every two links are connected by a pivot pin that allows rotation and translation of the links relative to each other. An angle sensor is mounted to at least one link proximate the pivot pin to allow for detection of the angle between the links. The ITML approach features less localizers than the individual transducer tracking design.

A third approach, referred to as the Rotating Transducer (RT) approach, involves using a single ultrasound transducer that is mounted to a carriage. The carriage traverses along a track located on the inner circumference of the brace. For example, the carriage may be moved along the tack by a string loop that is wrapped around the drive shaft of a motor. When the transducer reaches the motor, the rotation direction of the motor is changed and the transducer moves in the opposite direction. An inertia-based localizer is mounted to the transducer to track its motion. As the transducer rotates within the inner circumference of the brace, it collects data as to the outer circumferential topography of the bone surface. By using a single transducer, the RT approach includes the advantage of lower cost than the stationary transducer designs and higher accuracy due to the greater number of localized bone surface points for each tracking step, while maintaining a mechanical flexibility.

The system may include the vibration detection sensors including thin film accelerometers that detect the vibration produced by motion of the knee joint. Thin film accelerometers are used in lieu of sound sensors, because of better performance and less noise susceptibility. In some embodiments, the thin film accelerometers may utilize the same circuitry as is utilized for driving the accelerometers. The accelerometers are attached to the patients and communicatively connected to the orthopedic brace including the controllers in communication with the sensors.

Orthopedic Joint Prosthesis

An orthopedic joint prosthesis can include, but is not limited to, a prosthesis for a hip joint, wrist joint, elbow joint, finger joint, or knee joint. In some embodiments, an orthopedic joint prosthesis for a hip joint may include a preformed acetabular unit comprising a ball-socket-capsule unit. The manufacturer may make the preformed unit with different sized sockets and different sized balls. Thus, the physician need only size the socket and the stem to the patient's bone structure. The step of assembling the socket, matching the ball and the socket and affixing the capsule between the ball and the socket may be performed by the factory. This increases the strength of the bond between the capsule and the ball and socket as well as simplifies the overall operation.

The orthopedic joint prosthesis, e.g., a prosthetic hip joint, may include: a preformed acetabular unit comprising: (1) a socket adapted for attachment to an acetabulum; (2) a ball with a first attachment member, said ball rotatably positioned within said socket, said first attachment member facing outward away from said socket; and (3) a flexible joint capsule attached to said ball adjacent said first attachment member and to said socket, said capsule preventing wear debris from escaping from a joint between said ball and socket and preventing body debris from entering said joint and said capsule attached to said socket so as to avoid interference between the attachment of said socket to the acetabulum. For a total hip replacement, the prosthetic hip joint may further include: a femoral unit having a stem for attachment to a femur, and a second attachment member that mates with said first attachment member wherein said preformed acetabular unit is attached to said femoral unit by mating said first and second attachment members. Preferably, the mating of the first and second attachment members occurs after said preformed acetabular unit has been affixed to an acetabulum and said femoral unit has been affixed to a femur. See, e.g., U.S. Pat. No. 6,761,741, which is incorporated herein by reference.

PROPHETIC EXEMPLARY EMBODIMENTS

Example 1

A Hip Joint Apparatus that Includes an External Brace that Controls the Movement of the Artificial Hip Joint Prosthesis, Sensors to Detect Alignment of the Hip Joint Prosthesis and a Controller to Receive Signals from the Sensors and to Actuate the External Brace In a patient with arthritis, an artificial hip joint prosthesis is used to replace a hip joint in a patient having arthritis. The hip joint prosthesis has a femoral component which includes a head (or ball), a neck attached to the head and a stem which is implanted in the medullary canal. There is also an acetabular component which forms a socket that includes an outer and inner cup with the outer cup attached to the pelvic bone and the inner cup bearing the head of the femoral component. See FIG. 1. The neck and stem of the femoral component are made from titanium (See e.g., U.S. Pat. No. 6,761,741 issued to Iesaka on Jul. 13, 2004 which is incorporated herein by reference). For example, a femoral component with a titanium stem and a cobalt chromium alloy head is available from Stryker Orthopaedics, Mahwah, N.J.

An external orthopedic brace configured to align the hip joint prosthesis attaches to the pelvis and to the thigh of the patient. The external orthopedic brace is constructed with one or more force-applying elements, e.g., electrohydraulic actuators, linear hydraulic actuators, or rotational hydraulic actuators, to apply forces to align the hip joint prosthesis. The actuated orthopedic brace controls the motion of the hip joint prosthesis by applying forces to the femur and pelvis that promote alignment and/or restrict motion of the hip joint prosthesis. The brace is constructed from plastic and metal with Velcro™ hook straps to attach the brace at the waist and thigh of the patient. The electrohydraulic actuators include titanium actuator arms that apply forces to the hip joint and are attached to the aluminum external orthopedic brace with bolts. Methods and materials for external hip brace construction are described (see e.g., U.S. Pat. No. 6,589,195 issued to Schwenn et al. on Jul. 8, 2003 which is incorporated herein by reference). For example, an external hip joint brace with plastic and metal components is available from Orthomerica, Newport Beach, Calif. See e.g., Datasheet: Orthomerica Hip Orthotic which is incorporated herein by reference. To correct misalignment and to prevent dislocation of the hip joint prosthesis, electrohydraulic actuators on the brace apply forces to control adduction/abduction, flexion/extension, and rotation of the hip joint. External hip joint braces with actuator units apply force to a joint. See e.g., U.S. Pat. No. 7,507,215 issued to Ryan on Mar. 24, 2009; U.S. Patent Application Publication No. 2006/0200057 by Sterling published on Sep. 7, 2006; and Kobetic et al., *J. Rehabilitation Research and Development* 46: 447-462, 2009 which are incorporated herein by reference. Linear hydraulic actuators may be attached to the pelvis and thigh components of the external hip joint brace, and a rotational hydraulic actuator may be attached to the external hip joint brace laterally opposite the hip joint (see e.g., Kobetic et al. Ibid.). The external hip joint brace contains an electrohydraulic actuator system which includes a servoamplifier, a servovalve, a hydraulic power supply and an actuator. For example, a servoactuator with cylinders, feedback devices and servovalves in one assembly is available from Moog Inc., East Aurora, N.Y. 14052-0018. (See e.g., the Datasheet: "Moog, A085 Series Servoactuators" which is incorporated herein by reference). Sensors are configured to monitor the alignment of the artificial hip joint. The sensors signal a controller that activates a response from the electrohydraulic actuators to reposition the external hip joint brace.

Sensors in communication with controllers associated with the orthopedic brace are configured so that the orthopedic brace permits unrestrained motion of the hip joint prosthesis under a first set of alignment orientations and permits restrained motion of the hip joint prosthesis under a second set of alignment orientations. Ultrasound sensors are attached to the external hip joint brace to detect the alignment and orientation of the hip joint prosthesis and to signal the controller with data regarding alignment of the first component relative to the second component of the hip joint prosthesis. An ultrasound based system comprised of multiple transducers is used to determine the position and track the motion of the hip joint prosthesis. For example, pulse echo A-mode ultrasound transducers (e.g., immersion unfocused 3.5 MHz ultrasound transducers available from Olympus Corp., Waltham, Mass. are attached to the brace to localize points on joint surfaces. Ultrasound sensors positioned over the hip joint prosthesis, e.g., the acetabular component, the femoral component (e.g., the head, the neck, and the stem) and the proximal femur transcutaneously detect and localize the surfaces of the hip joint prosthesis and associated bones. The brace also is constructed with accelerometers to track the position of each ultrasound sensor, and in turn, the motion of the hip joint prosthesis. Sensors to track the position and motion of bone joints are described (see e.g., U.S. Patent Application Publication No. 2010/0198067 by Mahfouz et al. published Aug. 5, 2010 which is incorporated herein by reference). Signals from the ultrasound transducers and the accelerometers are transmitted wirelessly to a controller which is also attached to the brace.

The controller processes data from the ultrasound transducers and accelerometers to determine the alignment and orientation of the hip joint prosthesis, and signals the electrohydraulic actuators on the external hip brace to apply forces to the hip joint prosthesis as needed. Data from the ultrasound sensors and the accelerometer sensors are analyzed using a 3D model established for the hip joint prosthesis. Computer software models of bone joints may be utilized. See e.g., U.S. Patent Application Publication No. 2010/0198067, Ibid. A 3D model for a properly-aligned and functioning hip joint prosthesis for a patient of comparable size and stature is established from a database of ultrasound data obtained from previous patients and healthy controls. Moreover the patient's 3D model may be refined by using an orthopedic brace to acquire the position and structure of the patient's hip and leg bones prior to implantation of the hip joint prosthesis. The controller calculates the alignment and orientation of the hip joint prosthesis by comparison to the patient's personalized 3D model and monitors the change in alignment and motion of the hip joint prosthesis. The controller determines if the alignment of the hip joint prosthesis is within safe limits and signals to the hydraulic actuator to apply corrective force as needed. For example, lateral movement of the leg with the artificial hip joint beyond 45 degrees may increase risk for dislocation of the artificial hip joint. See e.g., "Artificial Hip Dislocation Precautions" (2012) by Fernley Physical Therapy at: http://www.fernleyphysicaltherapy.com/article.php?aid=328 which is incorporated herein by reference. Unsafe alignment of the femoral stem in the artificial hip joint is recognized by the controller which signals the hydraulic actuator to initiate a counter force to prevent further lateral movement and/or corrective movement to realign the femoral stem at a safe angle. The alignment and motion of the artificial hip joint is monitored by the external brace for approximately 3-6 months following implantation of the artificial hip joint. The ultrasound transducers, accelerometers, electrohydraulic actuators and the controller are empowered by a battery which is also attached to the external brace. For example, a 47.5 Watt-hour, NP-F970, 8.4 V lithium ion rechargeable battery available from Sony Corp. of America, New York, N.Y. may be used to power the brace. See e.g., Kobetic et al., J. Rehabilitation Research & Development 46: 447-462, 2009 which is incorporated herein by reference.

Example 2

An Orthopedic Apparatus to Prevent Dislocation of an Artificial Hip Joint Prosthesis that Includes a Hip Joint Brace with Sensors, an Electromechanical Actuator and a Controller A patient with an implanted artificial hip joint prosthesis is provided with an external orthopedic brace configured to align the hip joint prosthesis. The orthopedic brace contains sensors, one or more force-applying elements, e.g., electromechanical actuators, and a controller to prevent dislocation of the artificial hip joint. The implanted hip joint prosthesis has a femoral component that includes a head (or ball), a neck attached to the head and a stem which is implanted in the medullary canal, and an acetabular component which forms a socket that includes an outer and inner cup with the outer cup attached to the pelvic bone and the inner cup bearing the head of the femoral component. For example, a hip joint prosthesis with an acetabular component and femoral component is available from Stryker Orthopaedics, Mahwah, N.J. An external orthopedic brace with sensors, electromechanical actuators and a controller is attached to the patient's hip and thigh. The external orthopedic brace, in response to the sensors and controllers, detects and controls the position and alignment of the implanted hip joint prosthesis.

The external hip joint brace is constructed with sensors to detect the position, alignment and motion of the hip joint prosthesis. The hip joint brace is constructed from fabric with pockets to hold and affix the sensors and actuators to the brace. The external hip brace is constructed with a fabric sleeve, and force-applying elements. See e.g., U.S. Patent Application Publication No. 2006/0200057 by Sterling published on Sep. 7, 2006 which is incorporated herein by reference. Ultrasound sensors, e.g., pulse echo A-mode ultrasound transducers are used to localize selected surface regions on the hip joint prosthesis. For example, immersion unfocused 3.5 MHz ultrasound transducers available from Olympus Corp., Waltham, Mass. are attached to the hip joint brace and positioned over the hip joint prosthesis, e.g., opposite the acetabular component, the femoral component (e.g., the head, the neck, the stem) and the proximal femur. The ultrasound sensors transcutaneously detect and localize the surfaces of the hip joint prosthesis and associated bones of the pelvis and femur. In addition the orthopedic brace is constructed with accelerometers to track the position of each ultrasound sensor, and the motion of the hip joint prosthesis. Additional sensors positioned opposite ligaments and muscles of the joint detect flexion/extension of cartilage and muscle of the artificial joint. Ultrasound sensors and accelerometers are used to localize and track the motion of bone joints and surrounding ligaments and soft tissue. See e.g., U.S. Patent Application Publication No. 2010/0198067 by Mahfouz et al. published Aug. 5, 2010 and U.S. Pat. No. 5,533,519 issued to Radke et al. on Jul. 9, 1996 which are incorporated herein by reference. Signals from the ultrasound sensors and the accelerometers are transmitted wirelessly to a controller for processing. The controller signals to electromechanical actuators to apply forces to align the hip joint prosthesis.

The external orthopedic brace controls the movement and alignment of the artificial hip joint with electromechanical actuators that are affixed to the fabric brace and apply force to the hip joint. An actuator system with electrical motors that exert linear and rotational forces is attached in pockets in the fabric brace to allow force application to the hip joint prosthesis. For example, the electromechanical actuator system includes a three phase brushless electric motor from Hyperion with a peak power of approximately 388 watts (available from All e RC, L.L.C., Mesa, Ariz.) and a power source containing lithium polymer batteries providing a voltage of approximately 11.1 V and a capacity of 2640 maH (available from Emerging Power Inc., Hackensack, N.J.). In addition, the electromechanical actuator system contains gears, drive shafts and ball screws to convert rotational movement to linear movement. The actuators may be constructed from titanium and attached to the pelvic and thigh components of the hip brace to exert a linear force across the hip joint prosthesis to influence abduction/adduction and flexion/extension of the hip joint prosthesis. Actuators may also exert rotational forces on the brace through a hinge incorporated in the brace (see e.g., U.S. Pat. No. 5,421,810 issued to Davis et al. on Jun. 6, 1995 which is incorporated herein by reference). An electromechanical actuator system applies force to joints or artificial joint prostheses. See e.g., U.S. Pat. No. 8,058,823 issued to Horst et al. on Nov. 15, 2011 which is incorporated herein by reference. The actuators are controlled by a microprocessor controller attached to the external brace.

The microprocessor controller attached to the external brace processes data from the ultrasound transducers and accelerometers to determine the alignment of the hip joint prosthesis and signals an electromechanical actuator to apply force to the artificial hip joint prosthesis if necessary, e.g., upon misalignment of the ball and socket of the hip joint prosthesis or upon lateral movement of the femoral stem to an unsafe angle relative to the acetabular cup. Data from the ultrasound and accelerometer sensors are analyzed using a 3D model established for the artificial hip joint. Computer software models of bone joints and software to control a mechanical orthosis may be used in an orthopedic brace having a control system for a hip joint prosthesis. See e.g., U.S. Patent Application Publication No. 2010/0198067, Ibid. and Kobetic et al., *J. Rehabilitation Research & Development* 46: 447-462, 2009 which are incorporated herein by reference. A 3D model for a properly aligned and functioning hip joint prosthesis for a patient of comparable size and stature is established from a database of ultrasound and accelerometer data collected from cumulative patients fitted with external braces. Moreover the patient's 3D model may be refined by using an external orthopedic brace with sensors to track the position and alignment of the patient's pelvis and femur bones prior to implantation of the hip joint prosthesis. The controller calculates the alignment and orientation of the hip joint prosthesis by comparison to the patient's personalized 3D model and monitors the change in alignment and motion of the hip joint prosthesis over time. The controller determines if the alignment of the hip joint prosthesis is within safe limits and signals the electromechanical actuator to apply corrective force if necessary. For example, lateral movement of the leg may increase the risk for dislocation of the artificial hip joint. See e.g., the report: "Artificial Hip Dislocation Precautions" (2012) available from Fernley Physical Therapy, Fernley, Nev.; http://www.fernleyphysicaltherapy.com/article.php?aid=328 which is incorporated herein by reference. Lateral leg movement resulting in unsafe alignment of the artificial hip is detected by sensors on the brace. The ball and socket may be misaligned and the femoral stem may be at an unsafe angle relative to the acetabular cup of the orthopedic hip joint prosthesis. The controller, based upon sensor data or sensor signals, uses a 3D model to determine that the hip joint prosthesis is misaligned and signals the mechanical actuator to initiate a counter force by the orthopedic brace to prevent further lateral movement of the hip joint prosthesis and to initiate corrective movement to realign the ball and socket and the femoral stem of the hip joint prosthesis. After signaling to actuators to apply corrective forces the controller may prevent further movement of the realigned hip joint prosthesis, i.e., lock it in place, or apply intermediate forces to the hip joint prosthesis or release control of the hip joint prosthesis. Hip joint 3D computer models encoded in the controller may predict the preferred action by the orthopedic brace to avoid falling, stumbling, and hip dislocation by the patient.

Example 3

An Apparatus for an Artificial Hip Joint Prosthesis that Includes Inductive Sensors on the Artificial Hip Joint Prosthesis, Strain Sensors on the Hip Joint Ligaments, and an External Brace Surrounding the Hip Joint with a Controller and Actuators to Apply Forces to the Artificial Hip Joint Prosthesis In a patient with arthritis, an artificial hip joint prosthesis is used to replace a hip joint in a patient having arthritis. The hip joint prosthesis has a femoral component which includes a head (or ball), a neck attached to the head and a stem which is implanted in the medullary canal. There is also an acetabular component which forms a socket that includes an outer and inner cup with the outer cup attached to the pelvic bone and the inner cup bearing the head of the femoral component. The neck and stem of the femoral component are made from titanium. See e.g., U.S. Pat. No. 6,761,741 issued to Iesaka on Jul. 13, 2004 which is incorporated herein by reference. For example, a femoral component with a titanium stem and a cobalt chromium alloy head is available from Stryker Orthopaedics, Mahwah, N.J.

The external hip joint brace is constructed with inductive sensors embedded in the orthopedic hip joint prosthesis or in the surrounding tissue of the patient to detect the alignment and orientation of the hip joint prosthesis. Inductive sensors are comprised of a probe with inductive coils and a conductive target which is located a short distance away opposite the probe. Alternating current supplied to the inductive coil creates a magnetic field which induces small currents and an opposing magnetic field in the target of the inductive sensor. The electrical current induced in the target vary with the distance between the sensor probe and target, and conversely changes in the induced currents are used to calculate the distance between the target and the sensor probe. For example, inductive sensors, circuitry and algorithms to measure, calculate and report changes in position may be used. See e.g., TechNote: "Differences Between Capacitive and Eddy-Current Sensors" from Lion Precision, St. Paul, Minn. which is incorporated herein by reference. Data on sensor position is transmitted to a controller including a microprocessor to calculate the distance between the target and the probe. Multiple inductive sensors may be implanted to measure the position of the hip joint. For example inductive sensor probes may be implanted in the acetabular cup. Corresponding targets may be implanted in the femoral head to monitor the distance between the articular bearing surfaces. Inductive sensors may be embedded in a joint prosthesis. See e.g., U.S. Pat. No. 6,245,109 issued to Mendes et al. on Jun. 12, 2001 which is incorporated herein by reference. Signals from the implanted inductive sensors are transmitted wirelessly to a controller attached to the brace. The controller determines the alignment of the joint prosthesis by comparing the data from several inductive sensors to previous data sets from the patient or from another standard. For example, the distance between the femoral head and the acetabular cup may be compared to data for a normal alignment of the hip joint.

To monitor strain on the hip joint prosthesis, additional sensors are implanted in the soft tissues surrounding the hip joint prosthesis. Strain sensors with barbs that insert into soft tissues of the joint including ligaments and muscles are implanted at the time of hip joint replacement. For example, sensors with Hall effect strain transducers are implanted in the major hip ligaments, e.g., iliofemoral and pubofemoral, to monitor strain on the artificial hip joint. Implanted strain sensors with microbatteries are used to monitor strain in soft, peri-articular tissues and communicate with a controller. See e.g., U.S. Pat. No. 4,813,435 issued to Arms on Mar. 21, 1989 which is incorporated herein by reference.

An external orthopedic brace that attaches to the pelvis and to the thigh of the patient is constructed with a controller and one or more electrohydraulic actuators to apply forces to align the hip joint prosthesis. The brace is constructed of fabric and attaches to the hip and to the thigh over the hip joint prosthesis. Braces with actuator units apply force to a joint. See e.g., U.S. Patent Application Publication No. 2006/0200057 by Sterling published on Sep. 7, 2006; and Noel et al., *J. Neuroengineering Rehabilitation* 6: 16-27, 2009 which are incorporated herein by reference. The external hip joint brace contains an electrohydraulic actuator system that includes a servoamplifier, a servovalve, a hydraulic power supply and an actuator. For example, a servoactuator with cylinders, feedback devices and servovalves in one assembly is available from Moog Inc., East Aurora, N.Y. 14052-0018. (See e.g., the Datasheet: "Moog, A085 Series Servoactuators" which is incorporated herein by reference). The electrohydraulic actuator is sewn into the brace to hold it in place over the hip joint and to allow it to apply force to the artificial hip joint if necessary. The electrohydraulic actuator responds to a controller which is also attached to the external brace, and processes signals from the joint sensors.

The controller processes data from the inductive sensors and strain sensors to determine the alignment, orientation and strain on the hip joint prosthesis, and signals the electrohydraulic actuator system to apply forces to the hip joint prosthesis as needed. Data from the inductive sensors and strain sensors are analyzed using a 3D model established for the hip joint prosthesis. Empirical models of bone joints are described. See e.g., U.S. Patent Application Publication No. 2010/0198067, Ibid. A 3D model for a properly aligned and functioning artificial hip joint for a patient of comparable size and stature is established from inductive sensor data obtained from previous patients. Moreover the patient's 3D model may be refined by using data acquired from the patient when their hip joint is in a normal alignment. The controller calculates the alignment and orientation of the artificial hip joint by comparison to the patient's personalized 3D model and monitors the change in alignment and motion of the artificial joint. The controller determines if the alignment of the joint is within safe limits and signals the electrohydraulic actuator to apply corrective forces as needed. For example, lateral movement of the leg with a hip joint prosthesis may increase the separation between the femoral head and the acetabular cup and increase risk for dislocation of the artificial hip joint. See e.g., "Artificial Hip Dislocation Precautions" (2012) by Fernley Physical Therapy at: http://www.fernleyphysicaltherapy.com/article.php?aid=328 which is incorporated herein by reference. Unsafe separation distance between the femoral head and acetabular cup in the hip joint prosthesis is recognized by the controller which signals the hydraulic actuator to initiate a counter force to realign the femoral stem at a safe angle and reduce the separation of the hip joint components. The electrohydraulic actuators and the controller are empowered by a battery which is also attached to the external brace. For example, a 47.5 Watt-hour, NP-F970, 8.4 V lithium ion rechargeable battery available from Sony Corp. of America, New York, N.Y. may be used to power the brace (see e.g., Kobetic et al., *J. Rehabilitation Research & Development* 46: 447-462, 2009 which is incorporated herein by reference). The inductive sensors implanted in the hip joint are powered by a lithium ion battery which is also embedded in the hip joint prosthesis.

Example 4

A Brace for an Artificial Hip Joint Prosthesis with Remote Cameras to Detect Dangerous Movements of the Artificial Hip Joint Prosthesis and Signal Actuators on the Brace to Restrain the Hip Joint An actuatable brace system to control the movement of an artificial hip joint prosthesis is installed in a patient's home following total hip replacement surgery. The system includes an actuatable external brace that attaches to the pelvis and femur of the patient. The system also includes remote cameras located near the bed, recliner chair, car and stairs to monitor movement of the patient and of the artificial hip joint. The cameras signal wirelessly to the actuatable brace when the cameras detect that the orientation or alignment of the hip joint is unsafe. Electromechanical actuators activate the brace to control the motion of the artificial joint and to apply counterforces.

The actuatable brace controls the motion of a hip joint prosthesis by applying forces to the femur and pelvis which promote alignment and/or restrict motion of the hip joint prosthesis. The brace is constructed from plastic with Velcro™ hook straps at the waist and thigh to attach the brace. Metal actuator arms that apply forces to the hip joint are attached to the brace with bolts. See e.g., U.S. Pat. No. 6,589,195 issued to Schwenn et al. on Jul. 8, 2003 which is incorporated herein by reference. For example, a hip joint brace with plastic and metal components is available from Orthomerica, Newport Beach, Calif. See e.g., Datasheet: Orthomerica Hip Orthotic which is incorporated herein by reference. To prevent misalignment and dislocation of the artificial hip joint, actuators on the brace apply forces to control adduction/abduction, flexion/extension, and rotation of the hip joint. Actuators with electrical motors that exert linear and rotational forces may be attached to the brace. For example, the electromechanical actuator system may include a three phase brushless electric motor from Hyperion with a peak power of approximately 388 watts (available from All e RC L.L.C., Mesa, Ariz.) and a power source containing lithium polymer batteries providing a voltage of approximately 11.1 V and a capacity of 2640 maH (available from Emerging Power Inc., Hackensack, N.J.). In addition the actuator system may contain gears, drive shafts and ball screws to convert rotational movement to linear movement. The actuator system may be an electromechanical actuator system to apply force to joints. See e.g., U.S. Pat. No. 8,058,823 issued to Horst et al. on Nov. 15, 2011 which is incorporated herein by reference. For example, a linear actuator is attached to the brace at the thigh and at the waist to apply abduction and adduction forces to the members of the hip joint prosthesis. An abduction angle equal to or greater than 20 degrees is recommended for a sitting position. See e.g., Lima, Clinical Report: "Orthotic Management of Hip Dislocation" available from Orthomerica, Newport Beach, Calif. which is incorporated herein by reference. If the patient's thigh is at an angle less than 20 degrees from the patient's medial line, the actuator may apply a lateral force to increase the abduction angle. An actuator to also control flexion of the artificial hip joint may apply rotational force to a metal hinge which is attached laterally to the waist and thigh components of the brace. A metal hinge may limit flexion of the hip joint. See e.g., U.S. Pat. No. 5,421,810 issued to Davis et al. on Jun. 6, 1995 which is incorporated herein by reference. If the patient's hip joint flexion while seated is outside the range of 40-70 degrees it increases risk for dislocation of the hip joint. For example, if the flexion/extension angle is greater than 70 degrees the flexion/extension actuator may apply a force to reduce the angle to approximately less than or equal to 70 degrees. The actuators on the brace are activated by a controller on the brace that receives signals from remote cameras placed in the patient's home.

Cameras are placed in the patient's home at strategic locations to monitor the patient's movements and to monitor the hip joint alignment of the patient and to signal to the actuator system on the hip joint brace to actuate corrective alignment to the brace if misalignment or dangerous alignment is detected. The optical motion analysis system includes multiple high speed digital cameras placed near the stairs, the bed, the sofa or recliner and in the patient's car. An optical motion analysis system also includes reflective markers placed on the patient's hip, hip brace and leg, and motion analysis software. For example an optical motion analysis system may be NAC Hi-Dcam II Digital High Speed Camera Systems available from NAC Image Technology, Simi Valley, Calif. Real time measurements of hip joint flexion/extension angles and abduction/adduction angles are signaled by the optical motion analysis system. See e.g., Liu et al., *Proceedings of the 2010 IEEE International Conference of Information and Automation*, Harbin, China, pp. 179-184 which is incorporated herein by reference). For example, when the patient gets out of bed a camera near the bed may signal the patient's hip joint prosthesis abduction/adduction angle on a 1 second time scale to the controller on the hip joint brace. If the abduction angle falls below 20 degrees the controller may activate an actuator to apply an abduction force (i.e., extend laterally) to increase the angle to more than 20 degrees.

The controller on the artificial brace prosthesis is programmed to analyze the relevant motion analysis signals for each camera location and the patient's condition or positioning. For example, standing near the stairs, flexion/extension may be most important; when leaving your car both flexion and abduction may be important. Moreover, the controller may analyze the motion signals differently for a patient at risk of anterior hip dislocation versus a patient at risk of posterior hip dislocation. Hip joint extension may be most important for a patient at risk of anterior dislocation and the controller may restrict the angle of flexion/extension to prevent the last 40 degrees of hip extension. See e.g., Lima, Ibid.

The controller on the hip brace prosthesis is programmed to recognize and respond to normal, abnormal, and unsafe alignments and orientations of the artificial hip joint. For example, the controller recognizes the hip joint in a normal alignment with a flexion/extension angle between 0 degrees and 30 degrees for a walking patient. See e.g., Liu et al., Ibid. Under these conditions, the controller signals to the actuators to allow unrestrained motion of the hip joint. At a later time, the controller recognizes the hip joint flexion/extension angle is approximately 80 degrees, an abnormal angle for a walking patient. Under these conditions, the controller signals the actuators to apply a restraining force on the hip joint to reduce the flexion/extension angle to less than 30 degrees. For example the electromechanical actuator attached to the brace may apply a rotational force on the brace to reduce the flexion/extension angle to less than 30 degrees. If the controller detects a dangerous orientation of the hip joint, for example a flexion/extension angle of greater than 90 degrees which may indicate the patient is falling or unbalanced, then the controller can signal the actuator to apply a rotational force to immobilize the artificial hip joint. The controller includes algorithms to identify postural positions and hip joint alignments which are normal, abnormal and unsafe for the patient with an artificial hip joint (see e.g., Liu et al., Ibid.).

Example 5

A Brace for an Artificial Knee Joint Prosthesis that Includes Environmental Sensors on the Shoes to Detect Slipping, Stumbling and Falling of a Patient and to Signal to Actuators on the Knee Brace to Control the Alignment and Orientation of the Artificial Knee Joint Prosthesis A patient with an artificial knee joint prosthesis is fitted with an actuatable brace system to control alignment and movement of the knee joint prosthesis. The actuatable brace receives signals from the patient's shoes that may indicate imbalance, stumbling or impending falls by the patient. A controller on the brace analyzes the signals from the patient's shoes and activates actuators on the brace to apply forces to control the motion of the knee joint prosthesis. Based upon signals from the patient's shoes the controller calculates the predicted motion of the patient's leg and actuates counter forces or prevents further motion of the artificial joint and the corresponding leg.

A patient who has received a total knee replacement is fitted with an actuatable brace which controls the motion and alignment of the knee joint prosthesis. The actuatable brace includes an orthotic knee brace that attaches to the distal femur and proximal tibia. The orthotic knee brace is constructed with electrohydraulic actuators that control the flexion and extension of the knee joint prosthesis and rotation of the members of the knee joint prosthesis. For example, an orthotic knee brace that has an upper leg attachment and a lower leg attachment may be constructed from aluminum. See, e.g., 6061-T6 aluminum sheet available from OnlineMetals.com, Seattle Wash. To apply force to the knee joint prosthesis, hydraulic actuators may be fabricated from titanium and aluminum and attached to the knee brace with titanium fittings. For example, the knee brace may have actuators attached to the lateral and medial sides of the knee brace. See e.g., U.S. Pat. No. 7,507,215 issued to Ryan on Mar. 24, 2009, which is incorporated herein by reference. The actuators may include a hydraulic cylinder with a servo-valve and a 1000 psi pump that provides rapid controlled fluid flow to and from the cylinder. A controller signals to the actuators to apply forces to the artificial joint prosthesis that may be a push or pull to extend or flex the knee joint. The controller may be programmed with the maximum and minimum angles of flexion/extension for the knee joint prosthesis. If necessary, the controller may signal to the actuator to apply force to restore the knee joint to a permitted angle. For example, the knee joint flexion/extension angle may be between 0 degrees and 60 degrees for healthy adults walking in a straight line. See e.g., Liu et al., *Proceedings of the* 2010 *IEEE International Conference of Information and Automation*, Harbin, China, pp. 179-184 which is incorporated herein by reference. If the knee joint flexion/extension angle of the knee joint prosthesis is outside the permitted range, the controller may signal the actuator to apply a counterforce to bring the flexion/extension angle of the knee joint prosthesis within the normal range. Alternatively, the controller may signal the actuator to apply partial or complete resistance to movement of the knee joint prosthesis by restricting the flow of fluid in the hydraulic cylinder. For example, the controller may signal the actuator to "lock up" the knee joint and prevent further movement of the lower leg. The controller can receive signals from environmental sensors in the patient's shoes and can process the signals to detect unsafe movements and imbalances of the limb attached to the artificial knee joint. Models of limb motion and orientation may predict when the patient is going to fall or stumble and "lock-up" the knee joint to prevent a fall.

The environmental sensors may detect a change in an orientation of a patient's position in an environment and at the same time detect alignment orientations of the first component relative to the second component of the artificial knee joint prosthesis. The environmental sensors may detect the alignment orientations of the artificial knee joint prosthesis based upon detecting multiple alignment orientations of the orthopedic knee brace. Alternatively, the environmental sensors may detect the alignment orientations of the artificial knee joint prosthesis based upon detecting multiple alignment orientations of the first component relative to the second component of the artificial knee joint prosthesis. A shoe with sensors to detect motion and pressure is worn by the patient to detect unsafe movements of the knee joint and imbalances that may lead to stumbles and/or falls. Wireless systems for gait analysis and posture identification may be integrated into the shoe. See e.g., Bamberg et al., *IEEE Transactions on Information Technology in Biomedicine* 12: 413-423, 2008 and Sazonov et al., *IEEE Transactions on Biomedical Engineering* 58: 983-990, 2010 which are incorporated herein by reference. The shoe contains multiple sensors including: force-sensitive resistors, accelerometers, gyroscopes and electric field sensors to detect and analyze the gait of the patient by analyzing motion of the knee joint brace or the artificial knee joint prosthesis. Force-sensitive resistors (e.g., FSR-400 available from Interlink Electronics, Inc., Camarillo, Calif.) measure force distribution under the foot, e.g., heel strike and toe off. Accelerometers (e.g., ADXL203 available from Analog Devices, Inc., Norwood, Mass.) measure stride length and stride velocity; gyroscopes measure orientation, i.e., rotational position; and electric field sensors (e.g., MC33794 Proximity Sensor available from Freescale Semiconductor Inc., Austin, Tex.) which measure capacitance proportional to distance can measure the height of the foot above the floor. The sensors on the shoe signal wirelessly to the controller on the actuatable knee brace transmitting data regarding the movement of and pressure on the patient's feet as well as postural information. The shoe sensors may signal wirelessly to a receiver that is in communication with a controller. The controller can control movement of the brace based upon the signals received from the environment and from the positioning sensors on the brace or on the prosthetic orthopedic device. Alternatively the shoe sensor may be wired directly to the receiver and or the controller. The directly wired connection may communicate by conductive wire or by optical fiber. Software to identify gait patterns and postural information is encoded in the controller to evaluate the signals from the sensors on the shoe. Algorithms to may identify postural positions and recognize orientation and alignment of a limb. See e.g., Sazonov et al., Ibid. and Bamberg et al., Ibid.

The actuatable brace system may prevent a patient from stumbling or falling. The shoe sensors may detect imbalance and abnormal gait positions as well as unsafe postures that are signaled to the controller. The circuitry and software on the controller recognizes an unsafe position for the patient's leg and activates the actuators on the knee brace to apply force to the knee joint prosthesis to return the leg and the knee joint prosthesis to a safe position. Alternatively, the controller may activate valves in the hydraulic actuator to rapidly increase resistance to movement of the knee joint prosthesis. The resistance may immobilize the leg until a safe postural position or balance is indicated by the shoe sensors.

Each recited range includes all combinations and sub-combinations of ranges, as well as specific numerals contained therein.

All publications and patent applications cited in this specification are herein incorporated by reference to the extent not inconsistent with the description herein and for all purposes as if each individual publication or patent application were specifically and individually indicated to be incorporated by reference for all purposes.

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having ordinary skill in the art will recognize that there are various vehicles by which processes and/or systems and/or other technologies disclosed herein can be effected (e.g., hardware, software, and/or firmware), and that the preferred vehicle will vary with the context in which the processes and/or systems and/or other technologies are deployed. For example, if a surgeon determines that speed and accuracy are paramount, the surgeon may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies disclosed herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those having ordinary skill in the art will recognize that optical aspects of implementations will typically employ optically-oriented hardware, software, and or firmware.

In a general sense the various aspects disclosed herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices disclosed herein, or a microdigital processing unit configured by a computer program which at least partially carries out processes and/or devices disclosed herein), electrical circuitry forming a memory device (e.g., forms of random access memory), and/or electrical circuitry forming a communications device (e.g., a modem, communications switch, or optical-electrical equipment). The subject matter disclosed herein may be implemented in an analog or digital fashion or some combination thereof.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

The herein described components (e.g., steps), devices, and objects and the description accompanying them are used as examples for the sake of conceptual clarity and that various configuration modifications using the disclosure provided herein are within the skill of those in the art. Consequently, as used herein, the specific examples set forth and the accompanying description are intended to be representative of their more general classes. In general, use of any specific example herein is also intended to be representative of its class, and the non-inclusion of such specific components (e.g., steps), devices, and objects herein should not be taken as indicating that limitation is desired.

With respect to the use of substantially any plural or singular terms herein, the reader can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An apparatus comprising:
    an orthopedic brace adapted to be external to a subject, the orthopedic brace including a first member and a second member, wherein the first member is configured to control movement of a first component of an orthopedic joint prosthesis relative to the second member and the second member is configured to control movement of a second component of the orthopedic joint prosthesis;
    at least one of an imaging device, an inertial sensor, or a proximity sensor configured to detect a change in an orientation of the subject's position in an environment and at least one additional sensor configured to detect one or more alignment orientations of the first component relative to the second component of the orthopedic joint prosthesis by transcutaneously detecting at least one portion of the internal orthopedic joint prosthesis;
    one or more controllers in communication with the at least one of the imaging device, the inertial sensor, or the proximity sensor and the at least one additional sensor, wherein the at least one of the imaging device, the inertial sensor, or the proximity sensor reports the change in the orientation of the subject's position in the environment to the one or more controllers, and the at least one additional sensor reports the one or more alignment orientations to the one or more controllers, and the one or more controllers control movement of the first member relative to the second member of the orthopedic brace, wherein the orthopedic brace is configured to adjust the one or more alignment orientations of the first component relative to the second component of the orthopedic joint prosthesis; and
    one or more force-applying elements to control the movement of the first member relative to the second member, wherein the one or more force-applying elements in response to the one or more controllers are configured to permit unrestrained motion of the orthopedic joint prosthesis under a first set of the one or more alignment orientations and are configured to permit restrained motion of the orthopedic joint prosthesis under a second set of the one or more alignment orientations.

2. The apparatus of claim 1, wherein the second set of the one or more alignment orientations includes a separation of the first component relative to the second component of the orthopedic joint prosthesis.

3. The apparatus of claim 1, wherein the restrained motion comprises a motion from the second set of the one or more alignment orientations towards the first set of the one or more alignment orientations.

4. The apparatus of claim 1, wherein the restrained motion comprises a reduction of one or more alignment differences between the second set of the one or more alignment orientations and the first set of the one or more alignment orientations.

5. The apparatus of claim 1, wherein the at least one additional sensor comprises one or more sonic energy sensors.

6. The apparatus of claim 5, wherein the one or more sonic energy sensors comprise one or more ultrasonic sensors.

7. The apparatus of claim 6, wherein the one or more ultrasonic sensors are configured to determine a separation between the first component and the second component of the orthopedic joint prosthesis.

8. The apparatus of claim 6, wherein the one or more ultrasonic sensors are configured to determine a movement between the first component and the second component of the orthopedic joint prosthesis.

9. The apparatus of claim 1, wherein the at least one additional sensor is configured to detect one or more of positioning, disposition, attitude, or movement of the orthopedic joint prosthesis.

10. The apparatus of claim 1, wherein the one or more controllers are configured to be activated in response to a signal from the at least one of the imaging device, the inertial sensor, or the proximity sensor or the at least one additional sensor.

11. The apparatus of claim 1, comprising a power source.

12. The apparatus of claim 1, comprising a receiver configured to receive wireless signals from the at least one of the imaging device, the inertial sensor, or the proximity sensor or the at least one additional sensor.

13. The apparatus of claim 1, comprising a receiver configured to receive wire-based signals from the at least one of the imaging device, the inertial sensor, or the proximity sensor or the at least one additional sensor.

14. The apparatus of claim 1, comprising a transmitter configured to transmit a request for data from the at least one of the imaging device, the inertial sensor, or the proximity sensor or the at least one additional sensor.

15. The apparatus of claim 1, comprising the one or more controllers configured to use information from a model of one or more of a limb or a joint of the mammalian subject, wherein the one or more controllers are configured to predict future actions or consequences of movement of the brace.

16. An apparatus comprising:
    an orthopedic brace, the orthopedic brace including a first member and a second member, wherein the first member is configured to control movement of a first component of an orthopedic joint prosthesis relative to the second member and the second member is configured to control movement of a second component of the orthopedic joint prosthesis;
    at least one of an imaging device, an inertial sensor, or a proximity sensor configured to detect a change in an orientation of the subject's position in an environment;
    at least one additional sensor configured to detect one or more alignment orientations of the first component relative to the second component of the orthopedic joint prosthesis by transcutaneously detecting at least one portion of the internal orthopedic joint prosthesis; and
    one or more controllers in communication with the at least one of the imaging device, the inertial sensor, or the proximity sensor and the at least one additional sensor, wherein the at least one of the imaging device, the inertial sensor, or the proximity sensor reports the change in the orientation of the subject's position in the environment to the one or more controllers, and the at least one additional sensor reports the one or more alignment orientations to the one or more controllers, and the one or more controllers control movement of the first member relative to the second member of the orthopedic brace, wherein the orthopedic brace is configured to adjust the one or more alignment orientations of the first component relative to the second component of the orthopedic joint prosthesis via action of one or more force-applying elements, wherein the one or more force-applying elements in response to the one or more controllers are configured to permit unrestrained motion of the orthopedic joint prosthesis under a first set of the one or more alignment orientations and are configured to permit restrained motion of the orthopedic joint prosthesis under a second set of the one or more alignment orientations.

* * * * *